United States Patent
Kalantarov et al.

(10) Patent No.: US 12,070,490 B2
(45) Date of Patent: Aug. 27, 2024

(54) DEVELOPMENT OF DUAL WHOLE CELL-BASED VACCINE AGAINST PANCREATIC CANCER

(71) Applicant: THE TRUSTEES OF COLUMBIA UNIVERSITY IN THE CITY OF NEW YORK, New York, NY (US)

(72) Inventors: Gavreel Kalantarov, Fort Lee, NJ (US); Ilya Trakht, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 325 days.

(21) Appl. No.: 17/220,799

(22) Filed: Apr. 1, 2021

(65) Prior Publication Data
US 2021/0220458 A1 Jul. 22, 2021

Related U.S. Application Data

(62) Division of application No. 16/082,184, filed as application No. PCT/US2017/020589 on Mar. 3, 2017, now Pat. No. 11,020,465.

(60) Provisional application No. 62/303,965, filed on Mar. 4, 2016.

(51) Int. Cl.
| A61K 39/00 | (2006.01) |
| A61K 9/00 | (2006.01) |
| A61K 39/395 | (2006.01) |
| C07K 16/30 | (2006.01) |
| C12N 5/0784 | (2010.01) |
| C12N 5/0786 | (2010.01) |

(52) U.S. Cl.
CPC ........ *A61K 39/0011* (2013.01); *A61K 9/0019* (2013.01); *A61K 39/395* (2013.01); *C07K 16/30* (2013.01); *C12N 5/0639* (2013.01); *C12N 5/0645* (2013.01); *A61K 2039/5154* (2013.01); *A61K 2039/5158* (2013.01); *A61K 2039/54* (2013.01); *A61K 2039/545* (2013.01); *A61K 2039/575* (2013.01); *C12N 2500/44* (2013.01); *C12N 2501/22* (2013.01); *C12N 2501/2301* (2013.01); *C12N 2501/2304* (2013.01); *C12N 2501/2306* (2013.01); *C12N 2501/24* (2013.01); *C12N 2501/25* (2013.01)

(58) Field of Classification Search
CPC .............. A61K 39/0011; A61K 9/0019; A61K 2039/5154; A61K 2039/54; A61K 2039/545; A61K 2039/575; C12N 5/0639; C12N 5/0645; C12N 2501/2306; C12N 2501/24; A61P 35/00
USPC .................................................. 424/277.1
See application file for complete search history.

(56) References Cited

U.S. PATENT DOCUMENTS

| 5,635,188 A | 6/1997 | Bystryn |
| 5,788,963 A | 8/1998 | Murphy et al. |
| 6,440,735 B1 | 8/2002 | Gaeta |
| 6,498,034 B1 | 12/2002 | Strobl |
| 6,524,855 B2 | 2/2003 | Edelson et al. |
| 6,558,951 B1 | 5/2003 | Tomai et al. |
| 7,566,568 B2 | 7/2009 | Belardelli et al. |
| 7,781,213 B2 | 8/2010 | Waldmann et al. |
| 7,785,583 B2 | 8/2010 | Gilboa et al. |
| 7,846,446 B2 | 12/2010 | Cannon et al. |
| 7,959,934 B2 | 6/2011 | Klinman et al. |
| 7,981,673 B2 | 7/2011 | Adams et al. |
| 8,129,183 B2 | 3/2012 | Finocchiaro et al. |
| 8,232,100 B2 | 7/2012 | Waldmann et al. |
| 8,236,562 B2 | 8/2012 | Schuler et al. |
| 8,324,369 B2 | 12/2012 | Chen |
| 8,574,901 B2 | 11/2013 | Schuler et al. |
| 8,597,946 B2 | 12/2013 | Mule et al. |
| 8,613,916 B2 | 12/2013 | Masuyama |
| 8,614,093 B2 | 12/2013 | Kumon et al. |
| 8,741,639 B2 | 6/2014 | Yonemitsu et al. |
| 8,778,361 B2 | 7/2014 | Chu et al. |
| 8,921,104 B2 | 12/2014 | Waldmann et al. |
| 8,932,575 B2 | 1/2015 | Stone |
| 2006/0134067 A1* | 6/2006 | Liu ............. C12N 5/0639 435/459 |
| 2007/0212338 A1* | 9/2007 | Wagner ........ A01K 67/0271 435/346 |
| 2014/0037606 A1 | 2/2014 | Amiel |
| 2016/0058854 A1 | 3/2016 | Bender |

FOREIGN PATENT DOCUMENTS

| WO | WO 2013/016675 A1 | 1/2013 | |
| WO | WO-2013016675 A1 * | 1/2013 | ............. A61K 45/06 |

OTHER PUBLICATIONS

Rodrigues et al., The Role of T Lymphocytes in Cancer Patients Undergoing Immunotherapy with Autologous Dendritic Cells, 2011, Clinical Medicine Insights: Oncology 2011:5 107-115.
Matias et al., Influence of Immunotherapy with Autologous Dendritic Cells on Innate and Adaptive Immune Response in Cancer, 2013, Clinical Medicine Insights: Oncology 2013:7 165-172.
Cunha et al., Pattern response of dendritic cells in the tumor microenvironment and breast cancer, World Journal of Clinical Oncology, 2014, vol. 5, Issue 3495-502.

(Continued)

*Primary Examiner* — Yan Xiao
(74) *Attorney, Agent, or Firm* — Mark S. Cohen; Pearl Cohen; ZEDEK LATZER BARATZ LLP

(57) ABSTRACT

Disclosed herein is a different and novel approach to cancer vaccines using a subject's own dendritic cells (DC's) and macrophages (Mphs) in combination to present cancer antigens to the immune system. Further disclosed are methods of producing monocyte-derived autologous DCs and Mphs loaded ex vivo with particular whole irradiated cancer cells which generates optimally activated immunostimulatory antigen-presenting cells (APCs) as a superior method for stimulating robust and long-lasting immunity to a particular cancer in vivo as compared with more traditional vaccination methods. Compositions, methods of use and methods for preparation of these DC's and Mphs with cancer cells are also disclosed herein.

16 Claims, 6 Drawing Sheets

(56) References Cited

OTHER PUBLICATIONS

Aleixo et al., Dendritic Cell Vaccine and Cancer Treatment: New Patents, Recent Patents on Endocrine, Metabolic & Immune Drug Discovery 2014, 8, 26-29.
Wang et al., Immune Therapy in GI Malignancies: A Review, Journal of Clinical Oncology, 2015, vol. 33, No. 16, 1745-1753.
Le et al., "Safety and Survival With GVAX Pancreas Prime and Listeria Monocytogenes-Expressing Mesothelin (CRS-207) Boost Vaccines for Metastatic Pancreatic Cancer", 2015, 1325-1333.
Soares et al., "PD-1/PD-L1 blockade together with vaccine therapy facilitates effector T cell infiltration into pancreatic tumors", J Immunother, 2015, Jan. 38(1): 1-11.
Lutz et al., "Immunotherapy Converts Non-immunogenic Pancreatic Tumors into Immunogenic Foci of Immune Regulation", Cancer Immunol Res., 2014, 2(7): 616-631.
Salman et al., "Vaccine therapy for pancreatic cancer", OncoImmunology, 2013, 2:12, e26662.
Le et al., "Evaluation of Ipilimumab in combination with allogeneic pancreatic tumor cells transfected with a GM-CSF gene in previously treated pancreatic cancer", J Immunother., 2013, 36(7): 382-389.
Laheru et al., "Development of a Cytokine-Modified Allogeneic Whole Cell Pancreatic Cancer Vaccine", Methods Mol Biol., 2013, 980: 175-203.
Soares et al., "Vaccines for Pancreatic Cancer", Cancer J., 2012, 18(6): 642-652.
Lutz et al., "A Lethally Irradiated Allogeneic Granulocyte-Macrophage Colony Stimulating Factor-Secreting Tumor Vaccine for Pancreatic Adenocarcinoma: A Phase II Trial of Safety, Efficacy, and Immune Activation", Ann Surg., 2011, 253(2): 328-335.
Laheru et al., "Allogeneic GM-CSF Secreting Tumor Immunotherapy (GVAX®) Alone or in Sequence with Cyclophosphamide for Metastatic Pancreatic Cancer: A Pilot Study of Safety, Feasibility and Immune Activation", Clin Cancer Res., 2008, 14(5): 1455-1463.
Koido et al., "Treatment with Chemotherapy and Dendritic Cells Pulsed with Multiple Wilms' Tumor 1 (WT1)-Specific MHC Class I/II-Restricted Epitopes for Pancreatic Cancer", Clin Cancer Res., 2014, 20(16).
Koido et al., "Induction of antigen-specific cytotoxic T lymphocytes by fusion cells generated from allogeneic plasmacytoid dendritic and tumor cells", International Journal of Oncology 45, 2014, 470-478.
Koido et al., "Current Immunotherapeutic Approaches in Pancreatic Cancer", Clinical and Developmental Immunology, 2011, Article ID 267539, 15 pages.
Koido et al., "Dendritic/pancreatic carcinoma fusions for clinical use: Comparative functional analysis of healthy- versus patient-derived fusions", Clinical Immunology (2010) 135, 384-400.
McCormick et al., "Pancreatic cancer: Update on immunotherapies and algenpantucel-L", Human Vaccines & Immunotherapeutics, 2016, vol. 12, No. 3, 563-575.
Hardacre et al., "Addition of Algenpantucel-L Immunotherapy to Standard Adjuvant Therapy for Pancreatic Cancer: a Phase 2 Study.", J Gastrointest Surg, 2013, 17:94-101.
Dodson et al., "Potential targets for pancreatic cancer immunotherapeutics", Immunotherapy, 2011, 3(4): 517-537.
Pappalardo et al., "Induction of T-cell memory by a dendritic cell vaccine: a computational model", Bioinformatics, 2014, vol. 30, No. 13, 1884-1891.
Ricupito et al., "Boosting anticancer vaccines Too much of a good thing?", OncoImmunology 2:7, 2013, e25032.
Ricupito et al., "Booster Vaccinations against Cancer Are Critical in Prophylactic but Detrimental in Therapeutic Settings", Microenvironment and Immunology, 2013, Cancer Res; 73(12).
Forni et al., "Immunization in tumor prevention", International Immunopharmacology 3, 2003, 1151-1158.
Forni et al., "Vaccines for tumor prevention: a pipe dream?", 2015, J Infect Dev Ctries, 9(6), 600-608.
Tuohy et al., "Prophylactic Cancer Vaccination by Targeting Functional Non-Self", 2011, Ann Med., 43(5), 356-365.
Fontecha et al., "Dendritic Cell Migration to Peripheral Lymph Nodes", Handbook of Experimental 31 Pharmacology 188, 2009, 31-49.
Förster et al., "Lymph node homing of T cells and dendritic cells via afferent lymphatics", Trends in Immunology, 2012, vol. 33, No. 6.
Abediankenari et al., "Comparison of Several Maturation Inducing Factors in Dendritic Cell Differentiation", Iran.J.Immunol., 2010, vol. 7, No. 2, 83-7.
Mikyskova et al., "Dendritic cells pulsed with tumor cells killed by high hydrostatic pressure inhibit prostate tumor growth in TRAMP mice", Oncoimmunology, 2017, vol. 6, No. 12, e1362528, 10 pages.
Fucikova et al., "Phase I/II trial of dendritic cell-based active cellular immunotherapy with DCVAC/PCa in patients with rising PSA after primary prostatectomy or salvage radiotherapy for the treatment of prostate cancer", Cancer Immunol Immunother, 2018, 67:89-100.
Bloy et al., "Trial watch: Dendritic cell-based anticancer therapy", OncoImmunology, 2014, 3:11, e963424.
Truxova et al., "Day 3 Poly (I:C)-activated dendritic cells generated in CellGrofor use in cancer immunotherapy trials are fully comparable tostandard Day 5 DCs", Immunology Letters, 2014, 160, 39-49.
Chiang et al., "Whole Tumor Antigen Vaccines: Where Are We?", Vaccines, 2015, 3, 344-372.
Chiang et al., "Potential approaches for more successful dendritic cell-based immunotherapy", Expert Opinion on Biological Therapy, 2015, 15:4, 569-582.
Chiang et al., "A Dendritic Cell Vaccine Pulsed with Autologous Hypochlorous Acid-Oxidized Ovarian Cancer Lysate Primes Effective Broad Antitumor Immunity: From Bench to Bedside", Clin Cancer Res., 2013, 19(17), 4801-4815.
Kandalaft et al., "A Phase I vaccine trial using dendritic cells pulsed with autologous oxidized lysate for recurrent ovarian cancer", Journal of Translational Medicine, 2013, 11:149.
Nakamura et al., "Clinical Evaluation of Dendritic Cells Vaccination for Advanced Cancer Patients at Fukushima Medical University", J. Med. Sci., 2012, vol. 58, No. 1, 40-48.
Irisawa et al., "Endoscopic Ultrasound-Guided Fine-Needle Injection of Immature Dendritic Cells Into Advanced Pancreatic Cancer Refractory to Gemcitabine A Pilot Study", Pancreas, 2007, vol. 35, No. 2, 189-190.
Kanzaki et al., "Understanding the Response of Dendritic Cells to Activation by Streptococcal Preparation OK-432", Anticancer Research, 2005, 25, 4231-4238.
Hirschowitz et al., "Immunization of NSCLC Patients with Antigen-pulsed Immature Autologous Dendritic Cells", Lung Cancer, 2007, 57(3), 365-372.
Yannelli et al., "The large scale generation of dendritic cells for the immunization of patients with non-small cell lung cancer (NSCLC)", Lung Cancer, 2005, 47, 337-350.
Best et al., "Issues concerning the large scale cryopreservation of peripheral blood mononuclear cells (PBMC) for immunotherapy trials", Cryobiology, 2007, 54, 294-297.
Gilboa et al., "DC-based cancer vaccines", The Journal of Clinical Investigation, 2007, vol. 117, No. 5, 1195-203.
Gilboa et al., "Cancer immunotherapy with mRNA transfected dendritic cells", Immunological Reviews, 2004, vol. 199: 251-263.
Heiser et al., "Autologous dendritic cells transfected with prostate-specific antigen RNA stimulate CTL responses against metastatic prostate tumors", J. Clin. Invest., 2002, 109, 409-417.
Gilboa et al., "Immunotherapy of cancer with dendritic-cell-based vaccines", Cancer Immunol Immunother, 1998, 46, 82-87.
Nair et al., "Regression of Tumors in Mice Vaccinated with Professional Antigen-Presenting Cells Pulsed with Tumor Extracts", Int. J. Cancer, 1997, 70, 706-715.
Schlom et al., "Therapeutic Cancer Vaccines" Adv Cancer Res., 2014, 121, 67-124.
Amedei et al., "Pancreatic cancer: Role of the immune system in cancer progression and vaccine-based immunotherapy", Human Vaccines & Immunotherapeutics, 2014, 10:11, 3354-3368.
Nair et al., "Isolation and Generation of Human Dendritic Cells", Curr Protoc Immunol, 2012, 7, Unit7.32.

(56) References Cited

OTHER PUBLICATIONS

International Search Report and Written Opinion, International Patent Application No. PCT/US2017/020589, mailed May 18, 2017.
Berard F et al. Cross-Priming of Naive CD8 T Cells against Melanoma Antigens Using Dendritic Cells Loaded with killed Allogeneic Melanoma Cells, Journal of Experimental Medicine, Dec. 4, 2000, vol. 192, No. 11, p. 1535-1543; abstract p. 1536, 1st col. 3rd paragraph, p. 1536, 2nd col. 6th paragraph; p. 1537, $2^{nd}$ col. 1st paragraph.
Deer, EL et al. Phenotype and Genotype of Pancreatic Cancer Cell Lines, Pancreas, May 2010, vol. 39, No. 4 p. 125-435; p. 3, 2nd paragraph; DOI 10.1097/MPA.0b013e3181c15963.

\* cited by examiner

** - this is optional

FIG. 2
Prevention of Pancreatic Tumor Grafting in Mice by Prophylactic DC/CC

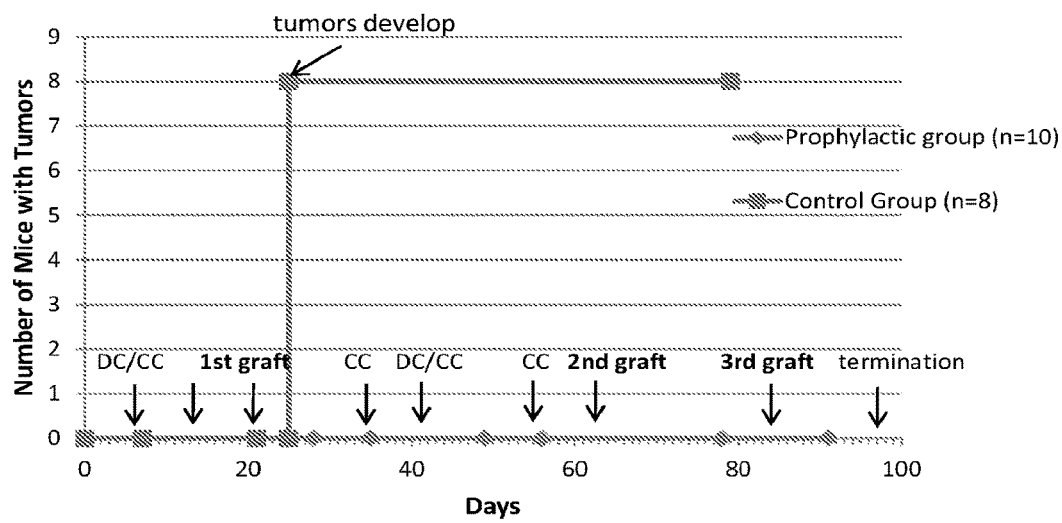

Arrows indicate injection of a vaccine or cancer cell graft

Mouse strain: C57Bl/B6
Sex: female
Age: 6-8 weeks
Graft: MMC13* mouse PaCa cells, $10^6$/mouse, s.c., right flank
Vaccine: autologous Dendritic cells, BM-derived, pulsed w/MMC13, 2x107, left flank, id and MMC13 cancer cells irradiated, $2x10^7$, left flank, i.d.

Abbreviations:
DC/CC dendritic cells pulsed with irradiated cancer cells
CC- irradiated cancer cells

* - MMC13 mouse PaCa cell line established form the PaCa metastases from Kras/p16/Pdx1-Cre (Kp16C)
mice (gift from Dr. Gloria Su)

FIG. 3
Elimination of Grafted Pancreatic Tumors in Mice after DC/CC vaccination

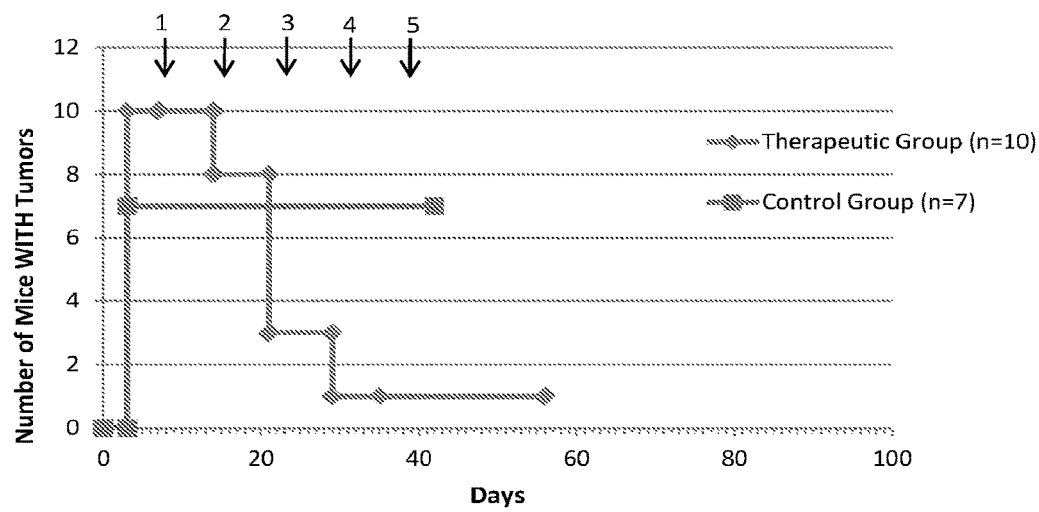

Arrows indicate injection of a vaccine:
1 - day 7, DC/CC (tumor size <3mm)
2 – day 17, DC/CC
3 – day 22, CC
4 – day 28, CC
5 – day 37, DC/CC Mouse strain: C57Bl/B6
Sex: female
Age: 6-8 weeks
Graft: MMC13* mouse PaCa cells, $10^6$/mouse, s.c, right flank
Vaccine: autologous Dendritic cells, BM-derived, pulsed w/MMC13, 2x107, left flank, i.d. and MMC13 cacner cells irradiated, $2x10^7$, left flank, i.d.

Abbreviations:
DC/CC dendritic cells pulsed with irradiated cancer cells
CC- irradiated cancer cells

* - MMC13 mouse PaCa cell line established form the PaCa metastases from Kras/p16/Pdx1-Cre (Kp16C)
mice (gift from Dr. Gloria Su)

ELISPOT analysis of IFN-γ Producing Splenic T-cells from Ectopic PaCa Mice
(representative pictures)

A - Tumor-grafted, non-vaccinated, pulsed;
B - Tumor-grafted, vaccinated, non-pulsed;
C - same as A, non-pulsed
D - non-grafted, control

FIG. 5

Kaplan-Meier analysis of the survival of mice vaccinated with DC/CC only or (DC+MPh)/CC cells prior to the engraftment with pancreatic cancer cells

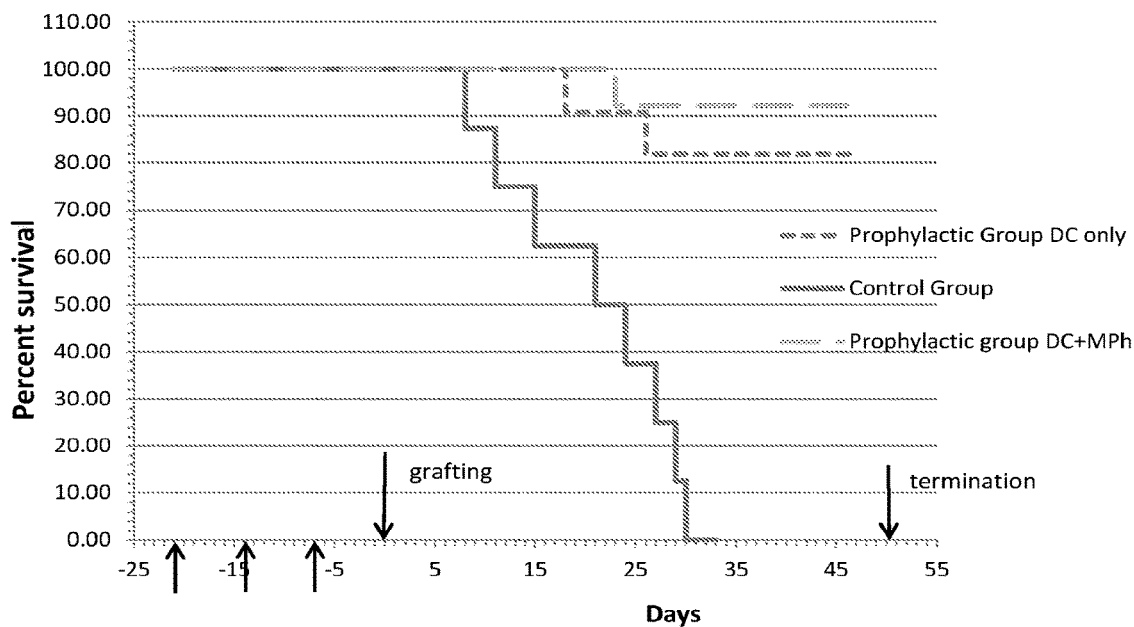

Arrows indicate injection of a vaccine:

1 - day - 21
2 – day - 14
3 – day - 7

Mouse strain: C57Bl/B6
Sex: female
Age: 6-8 weeks
Vaccine: autologous Dendritic cells, BM-derived, pulsed w/MMC13, $2 \times 10^7$, left flank, i.d. or DC/MPh cells pulsed with MMC13 cancer cells, $4 \times 10^7$, left flank, i.d.

Grafting was done with MMC13 cells, $5 \times 10^5$, right flank subcutaneously

FIG. 6

Kaplan-Meier analysis of the survival of mice with grafted pancreatic cancer cells after vaccination with DC/CC only or (DC+MPh)/CC cells

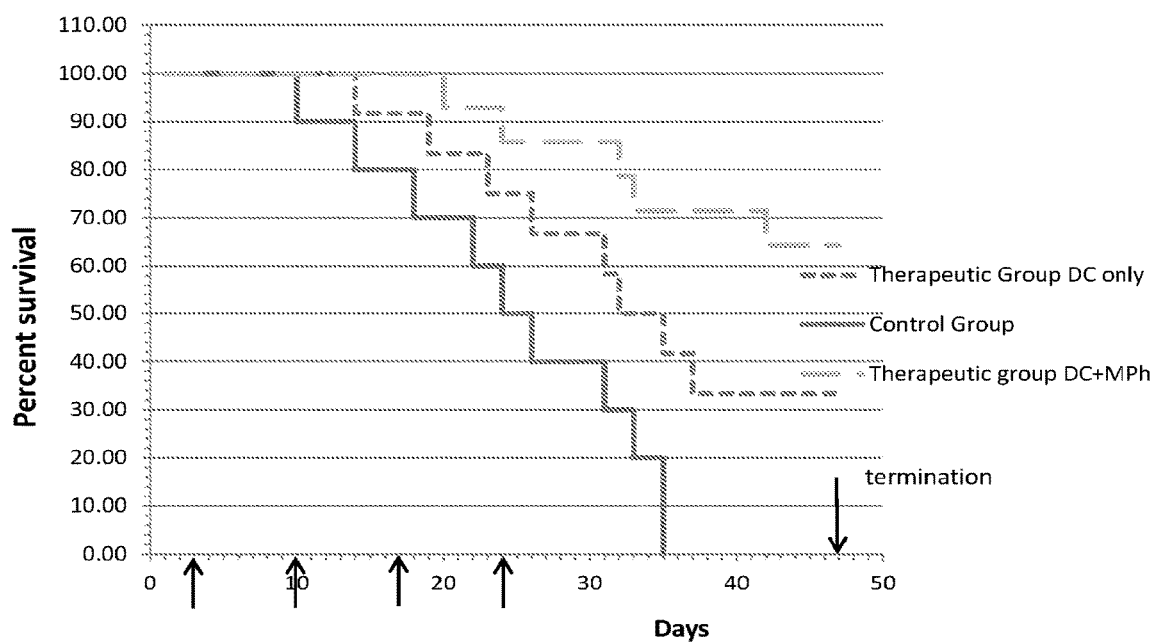

Arrows indicate injection of a vaccine:
1 - day 3
2 - day 10
3 - day 17
4 - day 24

Mouse strain: C57Bl/B6
Sex: female
Age: 6-8 weeks
Graft: MMC13* mouse PaCa cells, $5 \times 10^5$/mouse, s.c, right flank
Vaccine: autologous Dendritic cells, BM-derived, pulsed w/MMC13, $2 \times 10^7$, left flank, i.d. or DC/MPh cells pulsed with MMC13 cancer cells, $4 \times 10^7$, left flank, i.d.

DEVELOPMENT OF DUAL WHOLE CELL-BASED VACCINE AGAINST PANCREATIC CANCER

CROSS REFERENCE TO RELATED APPLICATIONS

This application is Divisional of Ser. No. 16/082,184, filed on Sep. 4, 2018 and now allowed, which is a National Phase Application of PCT International Application PCT/US2017/020589, filed Mar. 3, 2017 that claims priority to U.S. Provisional Patent Application 62/303,965, filed Mar. 4, 2016, each of which is incorporated herein by reference in its entirety.

BACKGROUND

One cancer vaccine approach that is gaining increasing popularity is the immunization of cancer patients with autologous, patient-derived dendritic cells (DCs) loaded with tumor antigens ex vivo. The underlying premise of this approach is that the efficiency and control provided by ex vivo manipulation of the DCs generates optimally activated antigen presenting cells (APC) and a superior method for stimulating immunity in vivo as compared with more traditional vaccination methods. Such methods include administering inactivated cancer cells, tumor cell lysates or tumor-specific antigens alone. However, DC-based vaccines face certain challenges. Namely, they have to be isolated in large quantities and manipulated into full maturation through several stages. They have to be loaded effectively with tumor antigens and conditioned towards populating germinal centers and engaging T cells in activation mode. An important role in all these stages is played by the inflammatory response. Unlike infectious pathogens, tumors do not induce an effective inflammatory response conducive to optimal activation of DCs, and as a result the ensuing immune response is weak and ineffective. The primary purpose of vaccinating individuals with cancer cells is to overcome this deficit by channeling tumor antigens into DCs and providing the conditions for their optimal maturation into potent immunostimulatory APCs.

Pancreatic ductal adenocarcinoma (PDA) is the fourth leading cause of death among cancer patients in the United States. Despite significant progress in understanding the mechanisms of this disease, PDA is still diagnosed mostly at late stage which makes the median 5-year survival rate between 5% and 25% depending on the stage of the disease. Surgical options are available only at very early stages of the disease and applicable to only 10-15% of newly diagnosed patients. Chemotherapy is only marginally effective as a treatment modality while other modalities such as immunotherapy are still in their infancy. Tumor cell-based vaccines offer a promising approach to boost the immune system and direct it to mount a response against cancer cells.

Given the poor prognosis of pancreatic cancer, novel therapeutic approaches are needed to improve survival. Cancer vaccines are designed to elicit an immune response against tumor-specific or tumor-associated antigens, encouraging the immune system to attack cancer cells bearing these antigens. Tumor antigen identification and its translation to immunotherapy still face many problems. Several trials of cancer cell vaccines, given alone or with other therapies, are currently enrolling patients with pancreatic cancer.

SUMMARY OF THE INVENTION

A different and novel approach to cancer vaccines using a subject's own dendritic cells (DCs) and macrophages (Mphs) in combination as a dual vaccine to present cancer antigens or fragments to the immune system has been discovered. It has now been found that monocyte-derived autologous DCs and Mphs loaded ex vivo with particular whole irradiated cancer cells administered to the subject generates optimally activated immunostimulatory antigen-presenting cells (APCs) as a superior method for stimulating robust and long-lasting immunity to the particular cancer in vivo as compared with more traditional vaccination methods. Compositions, methods of use and methods for preparation of these DCs and Mphs with cancer cells are also disclosed herein.

In one embodiment, the particular cancer cell is defined further as being a pancreatic cancer cell. One option for the antigen source for loading APCs includes whole attenuated or killed cancer cells, or a fragment, lysate or fraction thereof, preferably irradiated whole cancer cells. The whole cancer cells may be attenuated or killed by any of a variety of known methods. One method is the direct killing of the cell by chemical, mechanical and irradiation methods (e.g., gamma rays and ultraviolet radiation). Yet another embodiment includes the use or programmed cell death or apoptosis, which may also be used with embodiments of the present invention after irradiating the cells to increase their antigenicity.

Certain embodiments include a vaccine composition comprising both dendritic cells and macrophages loaded with attenuated or killed, whole cell cancer cells. The cancer cells can be autologous cells isolated from the subject if surgically removal of cells or tumor tissue is an available option, or they can come from other sources such as continuous human cell cultures that are of the same cancer type as the cancer in the intended recipient. Generally, the method and the composition will be formulated for administration of the isolated, loaded antigen-presenting cells to a patient.

Another embodiment includes a method of delivering whole cancer cells or a fragment, lysate or fraction thereof containing cancer antigen(s) to DCs and Mphs in vitro by contacting the DCs and Mphs with the whole cells or a fragment, lysate or fraction thereof for a time sufficient to allow the cancer cells or a fragment, lysate or fraction thereof to be internalized and processed for presentation on the DC/Mph cell surface. The DCs and Mphs may be human and the cancer cells may be human cells, e.g., cell lines, cells transformed to express a foreign cancer antigen, tumor cell lines, xenogeneic cells, or tumor cells, preferably autologous cells from the intended recipient of the vaccine. In a specific embodiment, the whole cancer cells are selected from the group consisting of the cell lines listed in Table 1, infra, and combinations thereof that have been attenuated or killed, for example, by chemical treatment, radiation, heat, cold, osmotic shock, pressure, grinding, shearing, ultrasound, drying, freeze spraying, puncturing, starving and combinations thereof. Any of the killed or attenuated cancer cells or cell fragments may be contacted with the DCs and Mphs for internalization. While the skilled artisan may have to adjust the exact ratios, one example of a common ratio of whole cancer cells to DC or Mphs is about 1:1, but can be 1:2 1:4, 1:6, 1:8, up to 1:10.

In further embodiment, provided is a cancer vaccine that includes cancer antigen-loaded dendritic cells and cancer antigen-loaded macrophages each autologous to a subject that has or is at risk of developing an identified cancer, wherein the cancer antigen-loaded dendritic cells and cancer antigen-loaded macrophages have internalized a whole cancer cell of the identified cancer or a fragment, lysate or fraction thereof in vitro. The cancer antigen-loaded dendritic cells or cancer antigen-loaded macrophages, or both, are, in certain embodiments, loaded with a full set of antigens for the identified cancer.

The whole cancer cell may be isolated from the identified cancer in the subject or obtained from a cancer cell line of the identified cancer. The cancer antigen-loaded dendritic cells and macrophages may be combined in a single formulation or separated into individual formulations. Examples of an identified cancer include, but are not limited to, melanoma, colon cancer, duodenal cancer, prostate cancer, breast cancer, ovarian cancer, ductal cancer, hepatic cancer, pancreatic cancer, renal cancer, liver cancer, sarcoma, endometrial cancer, testicular cancer, stomach cancer, dysplastic oral mucosa, polyposis, thyroid cancer, cervical cancer, head and neck cancer, invasive oral cancer, non-small cell lung carcinoma, small-cell lung cancer, mesothelioma, transitional and squamous cell urinary carcinoma, brain cancer, neuroblastoma, or glioma.

In a specific embodiment, the cancer vaccine is administered intradermally. The cancer antigen-loaded dendritic cells and cancer antigen-loaded macrophages may be combined in a single formulation or provided in separate formulations. The single formulation may be disposed in a containment device or separate formulations are disposed in two or more containment devices, which may optionally be used for administration.

Another embodiment pertains to a method of stimulating an immune response against a cancer cell-specific antigen in an identified cancer in a subject at risk of having or having the identified cancer, comprising co-administering an immunologically effective amount of cancer antigen-loaded dendritic cells and cancer antigen-loaded macrophages, each autologous to the subject, that have internalized a whole cancer cell of the identified cancer or a fragment, lysate or fraction thereof in vitro.

A further embodiment pertains to a method of treating cancer in a subject that has an identifiable cancer that involves co-administering a therapeutically effective amount of cancer antigen-loaded dendritic cells and cancer antigen-loaded macrophages, each autologous to the subject, that have internalized a whole cancer cell of the identified cancer or a fragment, lysate or fraction thereof in vitro.

In another embodiment, provided is a method of inducing an immune response against a cancer cell-specific antigen in an identified cancer in a subject having or at risk of having the identified cancer. The method involves the following steps:
(i) culturing a first population of white blood cells isolated from the subject under a first set of culture conditions that promote white blood cell differentiation into autologous dendritic cells and a second population of white blood cells isolated from the subject under a second set of conditions that promote differentiation into autologous macrophages;
(ii) isolating or obtaining cancer cells from the subject or from a cell culture of the identified cancer type, and attenuating or killing the isolated or obtained cancer cells;
(iii) contacting the attenuated or killed cancer cells with the autologous dendritic cells and macrophages, separately, in culture under conditions that permit the internalization of the cancer cells thereby producing cancer antigen-loaded dendritic cells and cancer antigen-loaded macrophages; and
(iv) co-administering the cancer antigen-loaded dendritic cells and cancer antigen-loaded macrophages to the subject in an immunologically effective amount. The cancer antigen-loaded dendritic cells are typically matured with one or more maturation factors prior to administering to the patient. Maturation factors useful for this purpose include, but are not limited to, monocyte conditioned medium, IFNα, IL-1β, IL-6 and TNFα.

The vaccine may be administered with one or more inflammatory and/or homing factors. Examples of inflammatory and/or homing factors includes LPS and polyI:C, for example.

BRIEF DESCRIPTION OF THE DRAWINGS

The following figures form part of the present specification and are included to further demonstrate certain embodiments of the present invention. The invention may be better understood by reference to one or more of these drawings in combination with the detailed description of specific embodiments presented herein.

FIG. 2 is a graph illustrating prevention of pancreatic tumor grafting in vivo via prophylactic administration of DC pulsed with irradiated MMC13 mouse pancreatic cancer (PaCa) cells derived from metastatic lesions of pancreatic cancer in genetically engineered mice (Kp16 mice carrying mutations in Kras oncogene and p16 protein), according to an embodiment;

FIG. 3 is a graph illustrating elimination of pancreatic tumor grafting in vivo via post-administration of DC pulsed with irradiated MMC13 mouse PaCa cells, according to an embodiment;

FIG. 4A represents tumor-grafted, non-vaccinated, pulsed; FIG. 4B represents tumor-grafted, vaccinated, non-pulsed; FIG. 4C represents tumor-grafted, non-vaccinated, non-pulsed; and FIG. 4D represents a non-grafted control, according to an embodiment;

FIG. 5 is a graph illustrating survival of mice vaccinated with DC pulsed with MMC13 cancer cells only or DC+Mph pulsed with MMC13 cancer cells prior to engraftment with pancreatic tumor cells, according to an embodiment; and FIG. 6 is a graph illustrating survival of mice with grafted pancreatic cancer cells after vaccination with DC pulsed with MMC13 cancer cells only or DC+Mph pulsed with MMC13 cancer cells, according to an embodiment.

DETAILED DESCRIPTION

Figure 1:
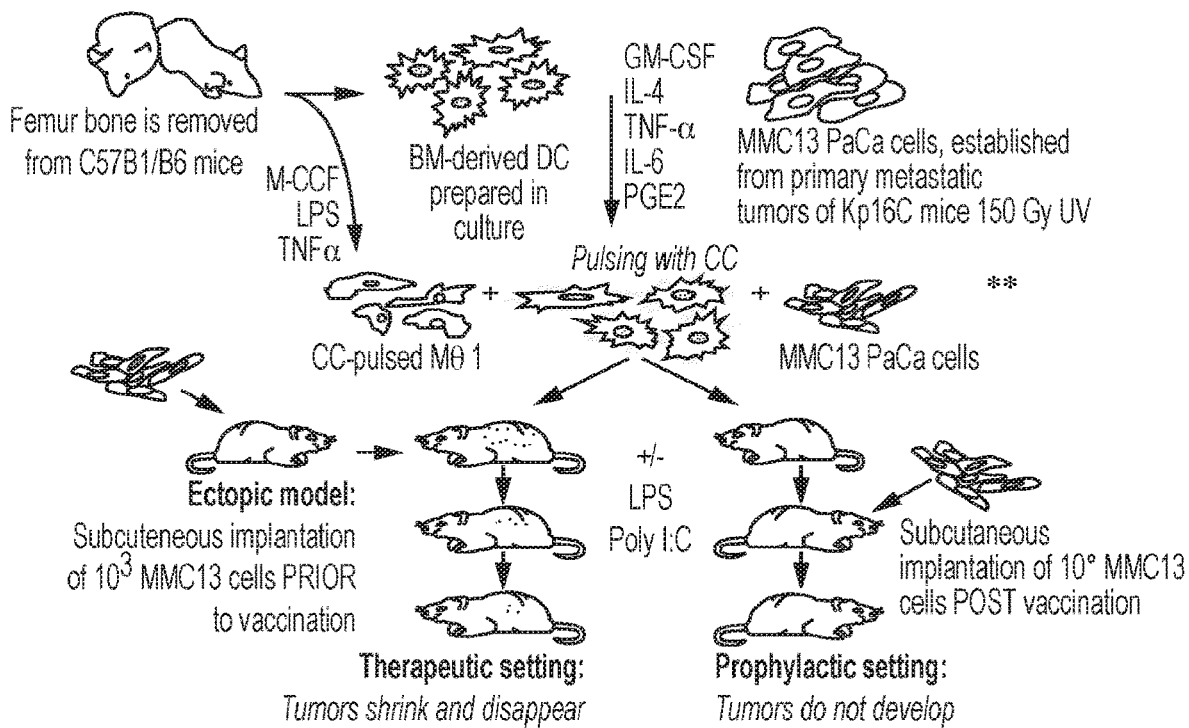
FIG. 1 is a schematic representation of a DC and whole cancer cell-based vaccine for pancreatic cancer, according to an embodiment.

It has now been discovered that the combination of both monocyte-derived autologous DCs and Mphs loaded ex vivo with attenuated or killed whole cancer cells or fragment(s), lysate or fraction thereof of an identified cancer to be targeted generates a powerful dual vaccine that optimally activates these immunostimulatory APCs against the targeted cancer. For convenience, when the term "whole cancer cells" is used, it includes cancer cell fragments, lysates or fractions; it is sometimes also expressed as whole cancer cells/fragments. This dual vaccine provides superior delivery of a full set of the cancer antigens for stimulating a robust and long-lasting humoral B cell and cellular T cell immune response in vivo as compared with more traditional vaccination methods that use far fewer antigens. Compositions, methods of use and methods for preparation of these DCs and Mphs with whole cancer cells/fragments are disclosed herein.

The present invention differs in several respects from similar approaches to treating cancer in general and pancreatic cancer in particular with vaccines that use DC pulsed with one or more individual tumor-associated antigens or peptides. By contrast, loading both DCs and Mphs with whole cancer cells provides a major advantage in that it allows for presentation of a broad spectrum of cancer antigens via internalization of the attenuated or killed cancer cells/fragments thereby activating the immune system against a wide range of tumor associated antigens from the particular cancer used for inoculation. Moreover, by engaging two major types of APCs, dendritic cells and macrophages, it is possible to cover a wider variety of antigen-presenting functions that occur both in germinal centers and in the peripheral capillary bed and interstitial areas to initiate a robust immune response to an identified cancer. Targeting the entire repertoire of tumor cell antigens by loading the APC with whole cancer cells/fragments dramatically reduces any possibility for the targeted cancer cells to evade the immune system.

In certain embodiments, compositions and methods for inducing immunity to cancer in a patient are provided by using isolated and purified autologous APCs (e.g., DCs and Mphs) primed by exposure to and internalization of whole cancer cells/fragments thereof. The APCs are preferably autologous APCs, e.g., DCs, and Mphs. Generally, the APCs are loaded with whole cancer cells that are isolated from the patient (autologous cells) who is the intended recipient of the vaccine, or another patient with the same type of cancer (allogeneic cells) and/or from a cancer cell line. In certain embodiments, loading APCs typically involves incubating either DC or DC+Mph isolated from the patient with the whole cancer cells to form "loaded APCs;" and then maturing the isolated, loaded APCs under suitable conditions. The APCs may be matured as described above or further with one or more maturation factors prior to administering to the patient. The skilled artisan will recognize that the APCs may be DCs and Mphs in various stages of maturation and the cancer cells may be internalized by the APCs as the APCs undergo maturation in the presence of one or more cytokines.

Several stages of manipulation of the APCs occur: (i) differentiation from monocytes into DC stimulated by such factors as GM-CSF and IL4 and into Mphs stimulated by factors such as macrophage colony-stimulating factor (M-CSF), lipopolysaccharide (LPS) and tumor necrosis factor alpha (TNF-α); (ii) maturation, of DC stimulated by a cocktail including for example TNF-α, IL-1β, IL-6, IFNα and $PGE_2$ for DC; and (iii) homing for DC stimulated by LPS and poly I:C, for example. In one embodiment, after exposure to whole cancer cells, or a fragment, lysate or fraction thereof for a duration of time that permits their internalization by the differentiated DCs, the cancer antigen-loaded DCs may be further matured, e.g., by exposure to one or more maturation factors for a sufficient time to induce the maturation of the DCs. The maturation step may include incubating DCs with at least one maturation factor that causes DCs to mature. Maturation factors useful for this purpose include, but are not limited to, TNFα, IL-1β, IL-6, $PGE_2$, and IFNα.

1. Overview

Tumor cell-based vaccines offer a promising approach to boost the immune system and direct it against cancer cells. The activation of the adaptive immune response against a specific target remains one of the most complex and sought-after goals in immunology. Dendritic cells and macrophages are involved in immune activation by processing and presenting antigens on both Major Histocompatibility Complex (MHC) class I and II molecules on their surface. A number of factors, genetic and environmental, affect the ability of the immune response to recognize and respond to processed antigens presented by APCs such as DCs and Mphs.

Pilot clinical trials involving DC vaccines administered to patients with non-Hodgkin's lymphoma or melanoma elicited some encouraging anti-tumor immune responses and tumor regression (Timmerman and Levy, Annu Rev Med, 50:507-529, 1999). Other clinical trials of DC-based vaccinations with autologous DCs pulsed with certain individual melanoma tumor-associated antigens have been conducted to assess the ability of these DC vaccines to induce clinical responses in melanoma cancer patients. As discussed in a review by Engell-Noerregaard et al. (Cancer Immunol Immunother, 58:1-14, 2009), 57 of 626 malignant melanoma patients (9%) showed an objective response when treated with DC-based vaccinations, but no significant correlations were noted between those objective responses and the tested parameters. Though DC-based vaccination therapies for cancer are viewed as having great potential to elicit a strong and broad immune attack to lessen the chance of tumor escape, this potential has not yet been realized, and so far has been shown to provide only a weak antitumor effect (Steven et al., Nature Medicine 10:909-915, 2004).

One of the problems typically associated with DC vaccines is that the administered DCs fail to migrate to lymphoid tissue (De Vries et al., Cancer Res, 63:12-17, 2003). Another problem with treating cancers by vaccine or immunotherapy is that the cancer often eludes the immune response. Accordingly, proper selection, delivery and processing of immunogenic, tumor-specific antigen targets by DCs are still key hurdles in developing any effective DC cancer vaccine.

Efforts have been made to develop DC-based cancer vaccines that involve DCs which have been loaded with tumor antigens in the form of peptides, proteins, tumor lysates, and mRNAs known to be expressed by the intended target cancer. Alternatively, DCs have been fused with target tumor cells or infected with viral vectors encoding the targeted tumor-associated antigens. Here we describe a novel new approach to making a dual cancer vaccine wherein (i) two different types of APCs, DCs and Mphs, are implemented in concert, and (ii) these APCs loaded with either killed or attenuated whole cancer cells/fragments to treat existing cancer in a subject by eliciting a strong immune response against the identified cancer in the subject, or are used as a dual vaccine to elicit a strong immune response to vaccinate against an identified cancer. To make the new dual vaccine, experiments were conducted targeting pancreatic cancer in a mouse model wherein DCs and Mphs cultured separately were loaded with whole killed or attenuated pancreatic cancer cells that provide for antigen presentation the full set of targeted tumor cell antigens thereby optimizing the subject's immune response to pancreatic cancer and minimizing the possibility that pancreatic cancer cells will evade the immune system response.

The rationale behind using both DC and Mph populations as APCs is based, at least partially, on the ground that they possess different mechanisms for invoking an immune response such that using both cell types in a dual approach provides a complementary effect that elicits a broader and more effective immune response that vaccination or treatment with either DC or Mph alone.

To facilitate the understanding of this invention, a number of terms are defined below. Terms defined herein have meanings as commonly understood by a person of ordinary skill in the areas relevant to the present invention.

2. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Kandel, Schwartz, and Jessell, eds., Principles of Neural Science, 4th ed., McGraw-Hill/Appleton & Lange: New York, NY (2000). Unless defined otherwise, all technical and scientific terms used herein have the same meaning as commonly understood by one of ordinary skill in the art.

Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The terms "animal," "patient," or "subject," as used herein, mean any animal (e.g., mammals, (including, but not limited to humans, primates, dogs, cattle, cows, horses, kangaroos, pigs, sheep, goats, cats, rabbits, rodents, and transgenic non-human animals), and the like, which are to be the recipient of a particular treatment. Typically, the terms "animal" "subject" and "patient" are used interchangeably herein in reference to a human subject or a rodent. The preferred animal, patient, or subject is a human.

As used herein, the terms "antigen-presenting cells" or "APCs" are used to refer to autologous cells that express MHC Class I and/or Class II molecules that present antigens to T cells. Examples of APCs include, e.g., professional or non-professional antigen processing and presenting cells. Examples of professional APCs include, e.g., B cells, spleen cells, lymph node cells, bone-marrow derived cells, monocytes, macrophages, dendritic cells, or non-fractionated peripheral blood mononuclear cells (PMBC). Examples of hematopoietic APCs include dendritic cells, B cells and macrophages. One of skill in the art will recognize that other APCs may be useful in the invention and that the invention is not limited to the exemplary cell types described herein.

The terms "loaded" or "loading" refer to the internalization of antigen into an APC. The APCs may be loaded with one or more individual antigens, or more preferably according to embodiments of the invention with whole cancer cells, and/or whole cell lysates or fractions thereof. In one embodiment, APCs loaded with whole cancer cells are capable of inducing an immune response that is characterized by the activation of CD4+ helper T cells, CD8+ cells, cytolytic T lymphocytes (cytolytic T cells or CTLs), and humoral B cells that are directed against a malignancy. Of course, the skilled artisan will recognize that other antigens may be used with the present invention and that the invention is not limited to the exemplary, whole cancer cells, cell clones, cell lines, cell supernatants, cell membranes, and/or antigens that are described herein.

As used herein, the terms "antigen-loaded dendritic cells" and "antigen-loaded macrophages (Mphs) refer to DCs and Mphs that have been loaded with antigen, for example, such as through internalization of whole cancer cells/fragments that have been attenuated or killed (e.g., such as by irradiation with gamma rays and ultra violet rays). Often, DCs and Mphs require a few hours, or up to a day, to process the antigen for presentation to naive and memory T cells. In some embodiments the DCs and Mphs are pulsed with antigen again after a day or two in order to enhance the uptake and processing of the antigen and/or provide one or more cytokines that will change the level of maturing of the DCs and Mphs. The antigen-loaded DCs or antigen-loaded Mphs are preferably loaded with at least a full set of antigens (as defined below).

The term "full set" as used herein with respect to cancer antigens loaded into DCs and Mphs refers to one or more antigens that are internalized and processed so as to present epitope containing fragments or pieces on the antigen-loaded DCs or antigen-loaded Mphs that are sufficient to induce a strong immune response to the target cancer cell. One of the discoveries reported herein is that the use of whole cancer cells/fragments to load DCs and Mphs with a full set of antigens for presentation results in an increased likelihood of generating DCs and Mphs that induce a sufficient immune response against the target cancer cell.

The term "an individual at risk" or "a subject at risk," as used herein, means one may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of cancer, such as a genetic profile indicating presence of cancer related genes, exposure to certain environmental hazards or lifestyle. An individual having one or more of these risk factors has a higher probability of developing cancer than an individual without these risk factors. Examples (i.e., categories) of risk groups are well known in the art and discussed herein.

The term "administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like.

As used herein, the term "autologous" is meant to refer to any material derived from the same individual to which it is later to be re-introduced into the individual. DCs or Mphs produced from autologous monocytes are derived from autologous cells and therefore are considered autologous.

The term "B cell" as used herein is defined as a cell derived from peripheral blood, lymph nodes, bone marrow and/or spleen. B cells can develop into plasma cells which produce antibodies.

The term "cancer" as used herein is defined as a hyperproliferation of cells whose unique trait—loss of normal control—results in unregulated growth, lack of differentiation, local tissue invasion, and/or metastasis. Examples include but are not limited to, melanoma, colon cancer, duodenal cancer, prostate cancer, breast cancer, ovarian cancer, ductal cancer, hepatic cancer, pancreatic cancer, liver cancer, sarcoma, renal cancer, endometrial cancer, testicular cancer, stomach cancer, dysplastic oral mucosa, polyposis, thyroid cancer, cervical cancer, head and neck cancer, invasive oral cancer, non-small cell lung carcinoma, small-cell lung cancer, mesothelioma, transitional and squamous cell urinary carcinoma, brain cancer, neuroblastoma, and glioma.

As used herein, the term "cancer cell" refers to a cell that exhibits an abnormal morphological or proliferative phenotype. The cancer cell may form part of a tumor, in which case it may be defined as a tumor cell. In this context, the term "tumor" as used herein means a malignant hypertrophy of tissues constituting certain organs or lumps and aggregates of cancer cells growing within these tissues, organs, or body cavities (e.g., the peritoneum or chest). In vitro, cancer cells are characterized by anchorage independent cell growth, loss of contact inhibition and the like, as is known to the skilled artisan. As compared to normal cells, cancer cells may demonstrate abnormal new growth of tissue, e.g., a solid tumor or cells that invade surrounding tissue and metastasize to other body sites. A tumor or cancer "cell line" is generally used to describe those cells that are immortal and that may be grown in vitro. A primary cell is often used to describe a cell that is in primary culture, that is, it is freshly isolated from a patient, tissue or tumor. A cell clone will generally be used to describe a cell that has been isolated or cloned from a single cell and may or may not have been passed in in vitro culture. The term "whole cancer cell" as used herein for internalization by DC and Mph includes fragments, lysates and fractions of the cancer cells.

As used herein, the term "cancer antigen" refers to antigen that is presented on the surface of cancer cells and may be specific, associated or over-expressed on such cancer cells. APC loaded with cancer antigen process the antigen and present on their surface pieces and/or fragments of the cancer antigen which include epitopes of the cancer antigen. The term "tumor antigen" is used interchangeably with cancer antigen.

The term "attenuated" as used herein in relation to treatment of whole cancer cells used for loading into APCs refers to any treatment that disrupts or weakens the treated cells. Attenuated cells may have a halt or reduction in cell division or decrease in any cellular metabolic processes needed to thrive.

As used herein, the terms "contacted" and "pulsed" and "exposed", when used in reference to a whole cancer cell or one or more antigens and APCs, are used herein to describe the process by which an antigen or whole cell is placed in direct contact with the APC such that the whole cancer cell or one or more antigens is internalized into the APC. Accordingly, the term "pulsed" is commonly used to describe the manner in which APCs are loaded. To achieve antigen presentation by the APC, the antigen is provided in an amount effective to "prime" the APCs to express antigen-bound MHC class I and/or class II molecules on the cell surface.

The term "co-administration" or "co-administering" as used herein refers to the administration of antigen-loaded dendritic cell(s) before, concurrently, or after the administration of antigen-loaded macrophage(s) such that the biological effects of either overlap.

As used herein, the terms "dendritic cell" or "DC" refer to all DCs useful in the present invention, that is, DCs in various stages of differentiation, maturation and/or activation. DCs may be derived from the subject (mostly from the peripheral blood) for which vaccine administration is intended. DCs may be used for either autologous or allogeneic application.

As used herein, the terms "macrophage" or "Mph" refer to all Mphs useful in the present invention, that is, Mphs in various stages of differentiation, maturation and/or activation. In one embodiment of the present invention, the Mphs are derived from the subject intended for vaccine administration because these cells are of autologous origin. However, in certain embodiments, the Mphs are derived from subjects intended for therapeutic vaccine administration and from healthy individuals, who are intended for preventive or prophylactic vaccine administration. In yet another embodiment, Mphs are used for either autologous or allogeneic application.

As used herein, the term "effective amount" refers to a quantity of antigen-loaded DCs and/or antigen-loaded macrophages that is sufficient to produce an intended biological effect.

As used herein, the term "immunologically effective amount" refers to an amount of antigen-loaded APCs that elicit a change in the immune response of a recipient against the antigen presented by the loaded APCs. The amount of antigen-loaded APCs inserted or reinserted into the patient will vary between individuals depending on many factors. For example, different doses may be required for an effective immune response in a human with a primary tumor or a metastatic spread.

As used herein, the term "irradiated," in the context of irradiating cancer cells for the present disclosure, is typically application of gamma-irradiation to the cancer cells, but also encompasses irradiation by x-rays, electrons, neutrons, protons, electromagnetic irradiation, visible light, ultraviolet light, and so on. In one aspect, the irradiation functions to prevent cell division of the cancer cells. In another aspect, the irradiation prevents cell division, but also denatures cellular proteins.

The term "kit" as used herein means any manufacture (e.g., a package or container) comprising at least one reagent, e.g., a dual DC+Mph whole cancer cell vaccine for treatment of cancer or a set of components to make such a vaccine. In certain embodiments, the manufacture may be promoted, distributed, or sold as a unit for performing the methods of the present invention.

The term "T cell" as used herein is defined as a thymus-derived cell that participates in cell-mediated immune reactions.

As used herein, the phrase "therapeutically effective amount" refers to the amount of antigen-loaded APCs that, when administered to an animal subject, is effective to kill, eliminate, or reduce cancer cells within the subject. The methods and compositions of the present invention are suitable for killing or reducing cancer cells both in vitro and in vivo.

As used herein, the term "vaccine" refers to compositions that affect the course of the disease by causing an effect on cells of the adaptive immune response, namely, B cells and/or T cells. The effect of vaccines can include, for example, induction of cell-mediated immunity or alteration of the response of the T cell to its antigen. Vaccine can be used for therapeutic administration or prophylactic administration.

3. Summary of Experimental Results and Embodiments of the Invention

The following is a summary of results of experiments described in the Examples and Detailed Description of Embodiments in this application.
  Pancreatic tumor grafting was prevented in vivo via administration of prophylactic autologous DCs pulsed with irradiated pancreatic cancer cells versus a control group;
  Pancreatic tumor grafts were eliminated in vivo post-administration of autologous DC pulsed with irradiated pancreatic cancer cells versus a control group;
  An increase in IFN-γ-secreting T-lymphocytes was seen in tumor-grafted mice that received vaccine including autologous DCs and Mphs pulsed with irradiated pancreatic cancer cells in comparison to non-vaccinated mice;
  Mice vaccinated with autologous DCs pulsed with irradiated pancreatic cancer cells only or with DCs+Mphs pulsed with pancreatic cancer cells prior to pancreatic tumor engraftment had higher survival rates compared with control; and
  Mice vaccinated with autologous DCs pulsed with irradiated pancreatic cancer cells or with DCs+Mphs pulsed with irradiated pancreatic cancer cells, after pancreatic tumor engraftment, had higher survival rates compared with control.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application (including reference lists) are hereby expressly incorporated by reference as if set forth herein in their entirety, except where terminology is not consistent with the definitions herein. Although specific terms are employed, they are used as in the art unless otherwise indicated.

4. Detailed Description of Embodiments

Methods of Preparing Dual Whole-Cell Vaccines Comprising Mphs and DCs

According to certain preferred embodiments, (i) autologous DCs and Mphs are extracted from a cancer patient who is the intended recipient of the vaccine, or alternatively, DCs and Mphs are generated from an extracted cell population from the intended recipient such as mononuclear leukocytes, (ii) each APC type (DC and Mph) is separately cultured and loaded with a full set of target cancer antigens via internalizing attenuated or killed whole cancer cells of the identified cancer or fragments, lysate or fraction thereof in vitro, and (iii) DCs are then matured by administering unique activation signals to permit the DC to mature before administration as a dual vaccine to the subject. Isolated macrophages, or macrophages differentiated from white blood cells, do not typically require further maturation. This ex vivo preparation ensures proper DC and Mph activation removed from the influence of the tumor environment or the immune-compromised cancer subject. When returned to the subject, the DCs and Mphs provide a dual vaccine that can then interact with B cells and T cells and initiate powerful anti-tumor immunity thereby inducing an immune response in subjects at risk of having cancer or treating existing cancer identified in the subject.

Accordingly, dual vaccine embodiments are typically autologous DCs and Mphs that are "pulsed" with attenuated or killed whole cancer cells (e.g. whole pancreatic cancer cells) ex vivo to permit cancer cell internalization, and, in the case of cancer antigen-loaded DCs, matured prior to administration to the subject. A person skilled in the art would also readily understand that an APC can be "pulsed" in a manner that exposes the APC to a whole cancer cell or cancer cell fragment for a time and under conditions sufficient to permit internalization of the cancer cell and presentation of the full set of cancer antigen fragments and epitopes on the surface of the APC.

In the case where the APC are pulsed in vitro, they can be plated on a culture dish and exposed to whole cancer cells, or fragments, lysates or fractions thereof and/or a selected group of individual antigens to be targeted by the immune system in a sufficient amount and for a sufficient period of time under conditions that allow the cells, cell fragments and/or antigens to be internalized into the APC and for the cancer antigen fragments and epitopes to be presented on its surface. The amount and time necessary to achieve internalization and surface presentation of the antigens to the APC may be determined by using methods known in the art or otherwise disclosed herein. Other methods known to those of skill in the art, for example immunoassays or binding assays, may be used to detect the presence of antigen on the APC following exposure to the antigen.

In certain embodiments, whole cancer cells are killed before loading into APCs. Cells can be killed by one of several methods, such as chemical killing using, e.g., betulinic acid, paclitaxel, camptothecin, ellipticine, mithramycin A, etoposide, vinblastine, vincristine, ionomycin and combinations thereof. Any of a number of methods or agents may be used to kill the whole cancer cells that serve as the antigen of the present invention, e.g., any or a wide variety of radiations (gamma, ultraviolet, microwaves, ultrasound, etc.), heat, cold, osmotic shock, pressure, grinding, shearing, drying, freeze spraying, freeze-drying, vacuum drying, puncturing, starving and combinations thereof. Another type of cell killing or death is referred to commonly as "apoptosis," which involves the activation of intracellular proteases and nucleases that lead to, for example, cell nucleus involution and nuclear DNA fragmentation. An understanding of the precise mechanisms by which various intracellular molecules interact to achieve cell death is not necessary for practicing the present invention.

The dual vaccine design provided in certain embodiments includes a subject's own (i.e. autologous) DCs and Mphs generated, for example, from white blood cells (WBCs) obtained from peripheral blood through a procedure called leukapheresis. During this procedure, the blood is pumped through a machine which separates red blood cells (RBCs) and WBCs. While RBCs are returned to a patient, the bulk of WBCs is collected and placed in cell culture dishes. The procedure is harmless to a patient since the depleted WBCs are quickly restored by the development of new WBCs in bone marrow.

WBCs in culture dishes are separated in two groups. One group is treated with cytokines and other factors which promote WBC differentiation into DCs, while a second group is treated with cytokines and factors promoting differentiation into Mphs. DCs and Mphs will typically be of autologous origin, i.e. originate from a subject who is considered for treatment or a subject who is in a high risk group for developing cancer and therefore being a candidate for preventive administration of a dual vaccine. Pancreatic cancer cells can be either isolated from the same patient (if surgically removed cancer cells or tumor tissue are available) or from other sources such as continuous human cell lines. The pancreatic cancer cells may be irradiated by gamma rays at levels in a range of from 150-200 Gy which makes them incapable to propagate and by UV which triggers apoptosis. Following this treatment the cancer cells are exposed to differentiated DCs and macrophages in culture.

In certain embodiments, allogeneic APCs may be used to induce the immunocompetence in a subject's immune cells. It is possible and may even be beneficial in certain cases, however, the histocompatibility and HLA match between MHC-I of donor's APC cells and TCR of recipient's T cells is highly desirable. Therefore, the use of autologous APC is a preferred embodiment. On the other hand, cancer cells may be autologous, allogeneic or even from established cell lines.

In certain embodiments, the risk of inducing an autoimmune response because of the presence of normal cells in an autologous sample of cancer cells used for loading is no higher than the risk of using cancer cells where no normal cells are present. This is because cancer cells express many antigens that are present on normal cells as well. Therefore, the risk of autoimmunity depends more on the dosing and timelines and also on the state of Tregs in a vaccinated person. The existing data show no indication that the significant autoimmune response can be induced by administering normal cells, normal antigens or APCs loaded with such. It can be explained most likely by the lack of presence of competent T cells which are mostly eliminated through clonal selection during neonatal stage.

TABLE 1

Cancer Cell lines For Loading APCs

| Cell Line name | Species | Tissue origin | Cell type | Disease |
|---|---|---|---|---|
| CFPAC-1 | Homo sapiens | Pancreas/ liver metastases | Epithelial | Ductal adenocarcinoma, cystic fibrosis |
| Capan-2 | Homo sapiens | pancreas | Mixed | adenocarcinoma |
| MIA-PaCa-2 | Homo sapiens | pancreas | Epithelial-like | carcinoma |
| BxPC3 | Homo sapiens | pancreas | Epithelial-like | adenocarcinoma |
| Hs766t | Homo sapiens | Pancreas/ lymph node | Epithelial | Pancreatic carcinoma |
| Panc 03.27 | Homo sapiens | pancreas | Epithelial | adenocarcinoma |
| Panc 02.13 | Homo sapiens | pancreas | Epithelial | adenocarcinoma |
| Panc 10.05 | Homo sapiens | pancreas | Epithelial | adenocarcinoma |
| Panc 10.05-GMCSF (GVAX) | Homo sapiens | pancreas | Epithelial | adenocarcinoma |
| Panc 05.04 | Homo sapiens | pancreas | Epithelial | adenocarcinoma |
| HPAC | Homo sapiens | pancreas | Epithelial | adenocarcinoma |
| HPAF-II | Homo sapiens | pancreas | Epithelial | adenocarcinoma |
| PANC-1 | Homo sapiens | Pancreas/ duct | Epithelial-like | Epithelioid carcinoma |
| PL45 | Homo sapiens | pancreas | Epithelial | Ductal adenocarcinoma |
| UACC-462 | Homo sapiens | pancreas | Epithelial-like | carcinoma |
| PANC 04.03 | Homo sapiens | pancreas | Epithelial | adenocarcinoma |

The maturation of DCs and Mphs is induced ex vivo by using appropriate growth and maturation factors in appropriate cell culture conditions or in vivo in conjunction with adjuvants that have been used to pretreat the cite of introduction into the subject. Theoretically, DCs and Mphs can be matured in vivo, but as mentioned above, DC maturation is only one of three important stages which are differentiation, maturation and homing. In vivo differentiation may be induced by injecting GM-CSF alone with the vaccine (not necessarily DC-based vaccine, but rather cancer cells alone, cancer cells lysates, proteins or peptides). Embodiments disclosed herein involve differentiation and maturation in vitro and homing of endogenous and administered DC in vivo. In a specific alternative embodiment, mature antigen-loaded APCs are administered in vivo and optionally administered in the presence of ligands for homing receptors, such as LPS and poly I:C. DCs and Mphs are able to recruit and interact with CD4+ T cells locally and activate both humoral (B cell) and cellular (CD8+ T cell) immune response against full set of target cancer antigens presented on their surface thereby targeting the cells.

Mouse Pancreatic Cancer Model

A mouse model of metastatic pancreatic cancer has been developed which can be easily monitored using serological assay. The mouse pancreatic cell lines that produce tumors in fully immunocompetent mice were transfected with His (6)-tagged mouse serum albumin (rMSA-His) readily secreted non-immunogenic protein. Such cells while preserving their tumorogenicity were secreting rMSA-His into mouse blood. Thus by testing the levels of MSA-His-6 in mouse serum it is possible to monitor the tumor dynamics without being dependent on visualization methods (Ultrasound, CT scan or, MRI) or a need to sacrifice the mouse. The cells can be inoculated i.v. or i.p. and allowed for their spread in the body generating metastases. Such model is more relevant to clinical picture in humans and eliminates the need of subcutaneous implantation of tumor cells. This described model presents a good opportunity for testing vaccine embodiments by simple serological testing, since the levels of MSA-His-6 reflect the total tumor burden. The dual vaccine described can 1 be evaluated using metastatic model and serological testing of tumor dynamics.

Monocytes are mononuclear leukocytes that are generated in bone marrow from myeloblast progenitors. These cells enter peripheral blood circulation and eventually migrate into tissues. Upon migrating to tissues, monocytes differentiate and mature and become specific cells that play important roles in the innate and adaptive immune systems, specifically they serve as precursor cells to macrophages and dendritic cells. Both Mphs and DCs are antigen-presenting cells that function by endo/phagocytosing, processing and presenting antigens to stimulate T cell activity.

As contemplated herein, embodiments involve use of whole cancer cells, or fragments, lysates or fractions thereof for loading into an APC to elicit an immune response against an identified (target) cancer. In alternative embodiments, individual tumor antigens (e.g. mesothelin) or antigenic tumor peptides or fragments of the foregoing may be used. Tumor antigens can be divided into two broad categories; shared tumor antigens; and unique tumor antigens. Shared antigens are expressed by many tumors, while unique tumor antigens can result from mutations induced through physical or chemical carcinogens, and are therefore expressed only by individual tumors. In certain embodiments, shared tumor antigens are loaded into the DCs and Mphs of the present invention. In other embodiments, unique tumor antigens are loaded into the DCs and Mphs of the present invention.

In the context of the present invention, "tumor antigen" (term used interchangeably with cancer antigen) refer to antigens that are common to specific hyperproliferative disorders. In certain aspects, the hyperproliferative disorder antigens of the present invention are derived from cancers, including but not limited to thymoma, sarcoma, liver cancer, melanoma, colon cancer, duodenal cancer, prostate cancer, breast cancer, ovarian cancer, ductal cancer, hepatic cancer, pancreatic cancer, renal cancer, endometrial cancer, testicular cancer, stomach cancer, dysplastic oral mucosa, polyposis, thyroid cancer, cervical cancer, head and neck cancer, invasive oral cancer, non-small cell lung carcinoma, small-cell lung cancer, mesothelioma, transitional and squamous cell urinary carcinoma, brain cancer, neuroblastoma, or glioma.

The tumor antigens and the antigenic cancer peptides thereof may be purified and isolated from natural sources such as from primary clinical isolates, cell lines and the like. The cancer peptides and their antigenic epitopes may also be obtained by chemical synthesis or by recombinant DNA techniques known in the arts. Techniques for chemical synthesis are described in Steward et al. (1969); Bodansky et al. (1976); Meienhofer (1983); and Schroder et al. (1965). Furthermore, as described in Renkvist et al. (2001), there are numerous antigens known in the art. Although analogs or artificially modified epitopes are not specifically described, a skilled artisan recognizes how to obtain or generate them by standard means in the art. Other antigens, identified by antibodies and as detected by the SEREX technology (see Sahin et al. (1997) and Chen et al. (2000)), are identified in the database of the Ludwig Institute for Cancer Research.

A. Macrophages

Current immunotherapies are primarily aimed at initiating or boosting T cell responses to tumors and their antigens. However, it is now also being increasingly realized that an immunosuppressive environment exists within tumors, induced by both cancer and immune cells, which inhibits the effect of cytotoxic T lymphocytes. As the effectiveness of immunotherapy may be limited by systemic and local tumor-induced immunosuppression, it has been realized that a second agent may be beneficial to alter the tumor microenvironment and/or decrease immune suppression.

Large phagocytic cells known as macrophages (Mphs) are found in stationary form in the tissues or as a mobile white blood cell, can serve in such a role. Mphs (and their precursors, monocytes) are the "big eaters" of the immune system. Mphs have been shown to eliminate malignant cells through the production of soluble factors (e.g., nitric oxide and TNFα) that can induce tumor cell apoptosis. Mphs can also eliminate cancer tumor cells through phagocytosis, based on their recognition of certain beacon molecules present on tumor cells. These cells reside in every tissue of the body, albeit in different guises where they engulf apoptotic cells and pathogens and produce immune effector molecules.

Mphs constitute a dominant fraction of the population of immune cells that infiltrate developing tumors. Recruited by tumor-derived signals, tumor-infiltrating macrophages are key orchestrators of a microenvironment that supports tumor progression. However, the phenotype of macrophages is pliable. It is reported herein that, if instructed properly, Mphs can mediate robust antitumor functions through their ability to eliminate malignant cells. Mphs are attractive targets for cancer immunotherapy because of their unique ability to regulate key elements of oncogenesis and tumor progression, including cancer cell viability and invasiveness, angiogenesis, and fibrosis. Because the activity of macrophages is dependent on microenvironmental signals, it is likely that many anticancer therapies that are designed to target malignant cells also impact the biology of macrophages.

For example, Mphs can reduce tumor-associated fibrosis, which is a key barrier against the delivery of chemotherapy. Thus, providing Mphs with anti-fibrotic properties may hold promise for facilitating the delivery of chemotherapy to neoplastic lesions. Because Mphs can rapidly debulk tumors, they may also be useful in downsizing tumors that were initially considered borderline for surgical resection. In addition, blocking CD47-SIRPα signaling may prime Mphs for enhancing antibody-based immunotherapies, as it facilitates the Fc receptor-mediated phagocytosis of antibody-coated cancer cells. Finally, shifting the phenotype of tumor-promoting Mphs may reverse many of the immunosuppressive mechanisms established within the tumor microenvironment and thus enhance the efficacy of T cell-based therapeutic approaches.

B. Dendritic Cells

DCs are white blood cells that acquire protein antigens from microbes or even cancerous cells and show, or "present" these antigens to T cells. The T cells, thus activated by the DCs, then initiate systemic immune responses to challenge the threat. DCs belong to the bone marrow-derived cell lineage, are present throughout the body in multiple tissues, and function as the central part of the mammalian immune system. Their main function is to process antigen material and present it on their surface to other cells of the immune system. Thus, DCs function as APCs, and they do so more efficiently than any other type of APC. DCs also act as messengers between innate and adaptive immunity, through a range of cell surface receptors that capture microbes and trigger information which is then transmitted to lymphocytes and cells of the innate immune system.

DCs are present in tissues that are in direct contact with the external environment, such as the skin (where there is a specialized dendritic cell type called Langerhans cells) and the inner lining of the nose, lungs, stomach and intestines. They can also be found in an immature state (iDC) in the blood. Once activated, they acquire the capacity to home or migrate to the lymph nodes where they interact with B cells and T cells to initiate and shape the adaptive immune response. At certain development stages, they grow branched projections, the dendrites, which give the cell its name.

In certain embodiments, DCs are derived from hematopoietic bone marrow progenitor cells, and these progenitor cells initially transform into iDCs. iDCs can be generated from monocytes, white blood cells which circulate in the body and, depending on the right signal, can turn into either DCs or Mphs. Monocytes are formed from stem cells in the bone marrow. In certain embodiments, monocyte-derived DCs can be generated in vitro from peripheral blood mononuclear cells (PBMCs). Plating of PBMCs in a tissue culture flask permits adherence of monocytes. Treatment of these monocytes with interleukin 4 (IL-4) and granulocyte-macrophage colony stimulating factor (GM-CSF) leads to differentiation to iDC in about a week. Subsequent treatment with tumor necrosis factor (TNF) further differentiates the iDC into mature DCs.

In other embodiments, methods used to generate DCs and Mphs may include culturing CD14+ monocytes in serum-free media in the presence of GM-CSF and IL-4. After a period of time (e.g., 5-7 days) in culture, the monocytes differentiated into iDC, which lose CD14 expression and express moderate to low levels of CD40 and the costimulatory ligands B7-1 and B7-2. These immature cells are characterized by high endocytic activity, in keeping with their efficient capture of antigens, and in this stage, their ability to activate T cells is still poor. This coincides with low expression of co-stimulatory molecules and limited ability to secrete certain cytokines. Immature dendritic cells constantly sample the surrounding environment for pathogens such as viruses and bacteria. This is done through pattern recognition receptors (PRRs) such as the TLRs. TLRs recognize specific chemical signatures found on subsets of pathogens and tumor tissue. Immature dendritic cells may also phagocytose small quantities of membrane from live cells.

Once they have come into contact with antigens or antigen source presented by the environment (such as microbes or tumor cells), immature dendritic cells are triggered to differentiate into mature dendritic cells and begin to migrate to the lymph nodes. In certain embodiments, DC maturation is accomplished by culturing the immature DCs for an additional 24-48 hours in the presence of several biological agents, including but not limited to, TNF, IL-6, IL-1β, and PGE$_2$. Immature dendritic cells phagocytose pathogens and degrade their proteins into small pieces, and upon maturation present those fragments at their cell surface using MHC molecules.

Simultaneously, the DCs up-regulate cell-surface receptors that act as co-receptors in T cell activation such as CD83, CD40 and others, thus greatly enhancing their ability to activate T cells. In certain embodiments, mature DCs further upregulate CD40, B7-1, and B7-2 and induce the de novo expression of the lymph node homing receptor CC chemokine receptor 7 (CCR7). In addition, they up-regulate, a chemotactic receptor that induces the DC to travel through the blood stream to the spleen or through the lymphatic system to lymph nodes. Here they act as antigen-presenting cells: they activate helper T cells and killer T cells as well as B cells by presenting them with antigens derived from pathogens or tumors, alongside non-antigen specific co-stimulatory signals.

Every T cell is specific to one particular antigenic peptide presented in MHC class I or II molecules, through receptors that are clonally expressed and are termed T cell receptors (TCRs). Only dendritic cells are able to activate resting naive T cells when the matching antigen-MHC complex is presented to their particular TCR. Other antigen-presenting cell types, such as macrophages and B cells, do not have the ability to trigger native resting T cells, and can only activate memory T cell. Because dendritic cells can activate both memory and naive T cells, they are often referred to as professional antigen-presenting cells, and they are the most potent of all the antigen-presenting cells.

DCs are constantly in communication with other cells in the body. This communication can take the form of direct cell-to-cell contact based on the interaction of cell-surface proteins. An example of this includes the interaction of the membrane proteins of the B7 family of dendritic cells, CD80 (B7.1) and CD86 (B7.2), with CD28 and CTLA4 on T cells. In addition, cellular communication of DC with their environment takes place over a distance via cytokines. For example, stimulating dendritic cells in vitro with microbial extracts causes the dendritic cells to rapidly begin producing IL-12. IL-12 is a signal that helps send naive CD4 T cells towards a Th1 phenotype. The ultimate consequence is priming and activation of the immune system for attack against the antigens which the dendritic cell presents on its surface.

DCs useful in the present invention include DCs at various differentiation stages (precursors, iDCs and mature DCs), DCs derived from blood precursors including but not limited to monocytes, dendritic cells derived from CD34-hematopoietic progenitor cells, subsets of DCs such as Langerhans cells, interstitial DCs and lymphoid DCs. In one embodiment, the DCs are monocyte derived dendritic cells (MDDCs), of human origin.

Dual DC/Mph Vaccine Administration and Dosage

Any vaccination regimen may be followed for use with the present invention, however, the following exemplary regimes have been used to great effect as will be known to those of skill in the art. One or more vaccination may be preceded or followed by the administration of additional whole cancer cell-pulsed APC by intervals ranging from seconds to hours to days to even weeks. In one embodiment, the whole cell-pulsed APCs and one or more lymphokines and/or cytokines are administered separately to the patient. Often, a significant period of time (1, 2, 3 or 4 weeks) is selected between the time of each immunization, such that the combination and/or overlap of two antigen-pulsed APCs exerts an advantageous effect on the recipient.

The frequency of vaccine administration may be individualized based on evaluating blood immune responses after the first vaccination. The presence of immune responses at such an early stage identifies patients that require less frequent vaccination, for example on a monthly basis. The absence of immune responses at this stage identifies patients that require more frequent vaccination, for example every other week. In the present invention, patients should be vaccinated for a life-time or until regression of malignancy. Similar protocol would be followed for prophylactic treatment. In the present invention, the comprehensive evaluation of elicited immunity against tumor antigens can be determined by any method known in the art.

Effective tumor killing may be measured before, during and/or after the initiation of the vaccination regimen. To achieve tumor cell killing, the whole cancer cell-loaded APCs are delivered to a patient in a combined amount effective to kill the tumor cells. These treatment cycles can be repeated multiple times, or delivered only once. The skilled artisan is aware that various factors are well known to influence patient response to vaccination, including, e.g., species, age, weight, gender, health, pregnancy, addictions, allergies, ethnic origin, prior medical conditions, current medical condition, treatment with anti-inflammatories, surgery, chemotherapy, radiotherapy and length of treatment. Thus, the skilled artisan understands the need to individualize dosage(s) to each patient and the various parameters that may easily be varied to achieve the optimal immune response, whether its cell killing (e.g., against cancer) or the reduction of an untoward immune response (e.g., cachexia)

The skilled artisan may also consider the condition that is to be treated prior to selecting the appropriate dosage. For example, a vaccination dosage that is appropriate for the treatment of a cancer may not be the desired dosage for subsequent surveillance therapy designed to prevent the recurrence of the cancer.

The dual-loaded APC vaccine approach may be used in conjunction or as part of a course of treatment that may also include one or more conventional cancer therapeutic treatments, including but not limited to, administration of chemotherapeutic agents, radiation therapy, hormone therapy, surgery and the like. It can also be combined with other immunotherapeutic modalities such as check-point inhibitors. For example, the skilled artisan will recognize that the present invention may be used in conjunction with therapeutically effective amount of pharmaceutical composition such a DNA damaging compound, such as, Adriamycin, 5-fluorouracil, etoposide, camptothecin, actinomycin-D, mitomycin C, cisplatin and the like. However, the present invention includes live cells that are going to activate other immune cells that may be affected by the DNA damaging agent. As such, any chemical and/or other course of treatment will generally be timed to maximize the adaptive immune response while at the same time aiding to kill as many cancer cells as possible.

The compositions and methods of use of the present invention are further illustrated in detail in the examples provided below, but these examples are not to be construed to limit the scope of the invention in any way. While these examples describe the invention, it is understood that modifications to the compositions and methods are well within the skill of one in the art, and such modifications are considered within the scope of the invention.

Administration frequency can be, e.g., once per week, twice per week, once every two weeks, once every three weeks, once every four weeks, once per month, once every two months, once every three months, once every four months, once every five months, once every six months, and so on. The total number of days where administration occurs can be one day, on 2 days, or on 3, 4, 5, 6, 7, 8, 9, 10, 11, 12, 13, 14, 15, 16, 17, 18, 19, or 20 days, and so on. It is understood that any given administration might involve two or more injections on the same day. In one aspect, the disclosure involves loading dendritic cells with whole tumor cells, where at least 10%, where at least 20%, at least 30%, at least 40%, at least 50%, at least 60%, at least 70%, at least 80%, at least 90%, at least 95%, or at least 99%, of the whole cancer cell that is loaded into the dendritic cells resides in whole tumor cells.

In non-limiting embodiments, the dual whole cell-based vaccine is held in a flask, in a vial, in a bottle, in a syringe, in a catheter, in a cannula, and so on. For administration, at least 20%, at least 30%, at least 40%, at least 50%, at least 60%, at least 70%, at least 80%, at least 90%, at least 95%, at least 99%, of the DCs in combination with Mphs that are administered are mature DCs and Mphs. Each dose may comprise about $10 \times 10^3$ DCs and Mphs, $20 \times 10^3$ cells, $50 \times 10^3$ cells, $100 \times 10^3$ cells, $200 \times 10^3$ cells, $500 \times 10^3$ cells, $1 \times 10^6$ cells, $2 \times 10^6$ cells, $20 \times 10^6$ cells, $50 \times 10^6$ cells, $100 \times 10^6$ cells, $200 \times 10^6$, $500 \times 10^6$, $1 \times 10^9$ cells, $2 \times 10^9$ cells, $5 \times 10^9$ cells, and $10 \times 10^9$ cells.

The antigen-loaded APCs may be administered subcutaneously, intracutaneously, intradermally, intravenously, intraarterially, intratumorally, parenterally, intraperitoneally, intramuscularly, intraocularly, intraosseally, epidurally, intradurally, and the like. Often, the most common routes of vaccination are subcutaneous (SC), intradermal (ID), intravenous (IV), intratumoral (IT) and intraperitoneal (IP). For DC/Mph-based vaccines intradermal injection is the most effective. The dermal layer of skin is rich in iDC, macrophages and T cells, therefore administering in vitro preconditioned APCs along with homing receptor ligands intradermally allows for additional recruitment of endogenous iDCs (Langerghans cells) and activation local Mphs and T cells. Such recruitment is also facilitated by the presence of inactivated cancer cells and their fragments in the vaccine composition, because during exposure of cancer cells to APCs, not all of them are engulfed and processed. Local inflammation causes local immunostimulation which later develops into a systemic immune response. This is much less likely to happen at intramuscular or even subcutaneous injection. To the extent that the vaccines are compatible with buffers and/or pharmacologically acceptable salts these can be prepared in aqueous solution suitably mixed with one or more additives. Under ordinary conditions of storage and use, these preparations may include limited amounts of a preservative and/or an antibiotic to prevent the growth of microorganisms.

The pharmaceutical forms suitable for injectable use include sterile aqueous solutions or dispersions. In all cases the form must be sterile and must be fluid. The storage conditions, if any, must be compatible with the delivery of stable DCs and Mphs under the conditions of manufacture and storage and must be preserved against the contaminating action of microorganisms, such as bacteria and fungi. In most cases, it may be common to include one or isotonic agents, for example, sugars or sodium chloride.

Sterile injectable solutions are prepared by incorporating the active compounds in the required amount in the appropriate solvent with various other ingredients enumerated above that may have been, e.g., filtered sterilization. Generally, dispersions are prepared by incorporating the various sterilized active ingredients into a sterile vehicle that includes a basic dispersion medium and the required other ingredients from those enumerated above. In the case of sterile powders for the preparation of antigens, the antigens may be pre-prepared and vacuum-dried, freeze-dried and/or freeze-sprayed to yield a powder of the active ingredient plus any additional desired ingredient from a previously sterile-filtered solution thereof.

As used herein, "pharmaceutically acceptable carrier" includes any and all solvents, dispersion media, liquid carriers, coatings, antibacterial and antifungal agents, isotonic and absorption delaying agents and the like. The use of such media and agents for pharmaceutical active substances is well known in the art. Except insofar as any conventional media or agent is incompatible with the cancer antigen, the agent may be used as part of the vaccine production process.

As used herein, the phrase "under conditions effective to allow protein complex formation" refers to those conditions and amounts of a irradiated, or killed, or otherwise processed tumor cells, tumor cell debris, processed tumor antigens, processed tumor cells, and/or antigens that are needed to "load" the MHC of an APC, e.g., a DC or Mph. As used herein, the term "suitable" for antigen loading are those conditions that permit a DC or Mph to contact, process and present one or more tumor antigens on MHC, whether intracellular or on the cell surface. Based on the present disclosure and the examples herein, the skilled artisan will know the incubation, temperature and time period sufficient to allow effective binding, processing and loading. Incubation steps are typically from about 6 to 48 hours, at a temperature of 37 degrees Celsius and 5% $CO_2$ in an APC suitable media supplemented with serum and other nutrients known in the art.

In one example of the present invention, the APCs are DCs and Mphs loaded with irradiated tumor cells, including but not limited to tumor cell lines and isolated autologous or allogeneic tumor cells. It is foreseeable that any tumor or cancer cells isolated from a patient or available from other sources may be used in an embodiment of the present invention. While the examples disclose use of pancreatic cancer cell lines, it is contemplated that an embodiment of the present invention may be used in the treatment of other cancers, and the type of cancer treatable by an embodiment of the present invention depends upon the type of cancer cells used to load the DCs and Mphs.

In certain embodiments, cancer cells used for loading the APCs are attenuated or killed prior to exposure to APCs. This is typically accomplished by treatment with gamma rays and ultraviolet rays. Although irradiation is used to induce apoptosis or cell death of the pancreatic cell lines used in the examples presented herein, other cell death inducing agents may be used in place of irradiation in an embodiment of the present invention. Other cell death inducing agents include but are not limited to paclitaxel, camptothecin, ellipticine, mithramycin A, etoposide, vinblastine and vincristine.

According to the present invention, the DCs and Mphs loaded with irradiated cancer cells are capable of inducing humoral B cells and eliciting cytotoxic cells (CTLs) which are able to kill tumor cells as well as target cells having tumor associated antigen derived peptides. The cytotoxic cells include but are not limited to CD8 T cells, natural killer cells (NK), and natural killer T cells (NKT). It is to be understood hereinafter that unless stated otherwise, reference to cytotoxic T cells refers to one or more of the cytotoxic cells.

According to the present invention, any incubation temperature and any amount of time of co-culture of the loaded DCs and Mphs that allows uptake of whole cancer cell by the DCs and Mphs can be used, as will be known to the skilled immunologist.

Methods of Treatment

Embodiments of the invention provide methods of treating, both prophylactically and therapeutically, subjects who belong to a high risk group for developing cancer or those who are already diagnosed with an identified cancer (e.g. pancreatic cancer), respectively. The methods of the present invention may include the treatment of a patient having a tumor by treating the patient with the cancer antigens of the present invention in an appropriate vector for vaccination, e.g., autologous DCs and Mphs loaded with irradiated whole cancer cells. The advantage of using a whole tumor cell approach is that the tumor antigens do not have to be prospectively identified and multiple antigens can be simultaneously targeted. In one embodiment, the patient is treated with DCs and Mphs loaded with irradiated whole cancer cells from the same patient. In another embodiment, the patient is treated with DCs and Mphs loaded with whole cancer cells (e.g. pancreatic cancer cells) isolated from continuous human cell cultures. In certain embodiments, the subject may treated with autologous T cells primed by autologous or allogeneic DCs and Mphs loaded with autologous or allogeneic irradiated whole cancer cells. A similar protocol would be followed for prophylactic treatment.

In certain embodiments, treatment of these conditions involves prophylactic vaccination. In FIG. 2, prevention of pancreatic tumor grafting in female C57Bl/B6 6-8 week old mice with prophylactic DCs without Mphs were pulsed with irradiated cancer cells is provided. Autologous DCs derived from bone-marrow were pulsed with $2\times10^7$ MMC13 cancer cells were injected intradermally into the left flank. MMC13 mouse pancreatic cancer cells, $10^°$/mouse, were administered subcutaneously into the right flank of the mouse in an effort to generate a tumor. In a control group, $2\times10^7$ MMC13 irradiated cancer cells were injected intradermally into the left flank. Tumors developed in the control group in all eight mice where prophylactic administration prevented tumor development.

FIG. 5 provides an analysis of the survival of mice vaccinated with DCs alone pulsed with irradiated cancer cells prior to the engraftment of $5\times10^5$ MMC13 pancreatic cancer cells. Or DCs and Mphs pulsed with MMC13 cancer cells were also provided in FIG. 5. A vaccine comprising autologous DCs derived from bone marrow and pulsed with $2\times10^7$ MMC13 irradiated cancer cells was injected intradermally into the left flank of a 6-8 week old female C57B1/B6 mouse. Or, a vaccine comprising autologous DCs and Mphs pulsed with $4\times10^7$ MMC13 cancer cells was injected intradermally into the right flank intradermally. Injection of the vaccine occurred at day 7, at day 14, and at day 21 prior to engraftment. A 100% survival post grafting in the prophylactic DC only group at day 15 dropped to an 80% survival rate at day 45. On the other hand, a 100% survival post grafting in the prophylactic group DC+Mph dropped to a 90% survival rate at day 45.

In other embodiments, treatment involves therapeutic vaccination. In FIG. 3, elimination of grafted pancreatic tumors in female C57BI/B6 6-8 week old mice with DCs without Mphs were pulsed with irradiated cancer cells is provided. MMC13 mouse pancreatic cancer cells, $10^°$/mouse, were administered subcutaneously into the right flank of the mouse in an effort to generate a tumor. Autologous DCs derived from bone-marrow were pulsed with $2\times10^7$ MMC13 cancer cells and were injected intradermally into the left flank. As a control, $2\times10^7$ MMC13 irradiated cancer cells were injected intradermally into the left flank. DC vaccine was injected at day 7, day 17, and day 37 where the irradiated cancer cells (CC) only were injected at day 28 and day 37. Tumors developed shortly after in the control group in all seven mice for 40 days. Where prophylactic DC/CC vaccine was administered in the therapeutic group of 10 mice after engraftment, tumor development was eliminated in 9 of 10 mice after 50 days.

FIG. 6 provides an analysis of the survival of mice vaccinated with DCs alone pulsed with irradiated cancer cells after the engraftment of $5\times10^5$ MMC13 pancreatic cancer cells. Or DCs and Mphs pulsed with MMC13 cancer cells after the engraftment of MMC13 pancreatic cancer cells were also provided in FIG. 6. A vaccine comprising autologous DCs derived from bone marrow and pulsed with $2\times10^7$ MMC13 irradiated cancer cells was injected intradermally into the right flank of a 6-8 week old female C57B1/B6 mouse. Or, a vaccine comprising autologous DCs and Mphs pulsed with $4\times10^7$ MMC13 cancer cells was injected intradermally into the left flank intradermally. Injection of the vaccine occurred at day 3, at day 10, day 17 and at day 24 after engraftment. At day 45, 70% of the mice survived with DCs+Mphs vaccine where only approximately 30% of the mice survive with DCs alone.

Without being bound by theory, in certain embodiments, a synergistic response occurs. Mphs are APCs of local action, meaning that they can recruit competent T cells (as well as memory T cells) locally without a requirement migrate to germinal center to do so. As for the synergistic effect, activated Mphs are known to secrete a number of cytokines (TNF-α, IL-2, IL-4 which cause differentiation of monocytes into DC and most important the maturation of iDC. Therefore, they well may recruit endogenous iDC on the site of injection as well as enhance the expression of costimulatory molecules on already mature DC which are co-administered with them. That would comprise the synergistic effect.

Other embodiments are set forth in the summary of the invention, or described in the examples below.

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Methods and Materials

Preparation of Murine Pancreatic Cancer Cells

Both MC-1 and MMC-13 tumor cells at $3 \times 10^5$/ml seeding density were grown in culture-treated dishes in 30 mL of c-DMEM until 90% confluency at 37 degrees C. for about 80 hours, detached and collected with EDTA, washed twice with sterile PBS, and then irradiated in $Co^{60}$-based irradiator at 150 Gy to render the cells incapable of propagating. Following irradiation, the cells were exposed to UV light in a CV-1000 UVP chamber for 5 seconds to induce apoptosis. Irradiated cells served as a source of cancer antigens for pulsing differentiated DC and Mph.

Reagents

The recombinant cytokines used were GM-CSF (conditioned culture media of mouse myeloma cell line J-558L transfected with mouse GM-CSF, gift of Dr. Raphael Clynes, and mouse recombinant GM-CSF from In Vitrogen, PMC2016), IL-4 (Sigma, 11020), IL-6 (Sigma), TNF-α (In Vitrogen, PMC3034) AND $PGE_2$ (Sigma) For homing stimulation we also used LPS (Sigma) and poly I:C (Clontech).

Generation of Tumors In Vivo

MMC-13 pancreatic cancer cells ($10^0$/mouse) established from primary metastatic tumors of 6-8 months old Kp16C female mice, were maintained in cell culture and were collected from culture dishes using 0.25% trypsin. The cells were washed in sterile PBS 3 times, counted, and $5 \times 10^3$ cells were injected into the right flanks of C57BI/B6 mice subcutaneously or intraperitoneally in 100 μl of saline. Tumors were monitored starting from day three using caliper measurements.

Example 2: Isolation of Mphs and DCs from Mouse Bone Marrow Monocytes

Bone marrow monocytes were isolated by flushing femurs of mice with DMEM media supplemented with antibiotics, non-essential amino acids, sodium pyruvate, vitamins and 10% FBS (complete DMEM or c-DMEM). Cell aggregates were dislodged by gentle pipetting with subsequent passaging of cell suspension through a 100 um nylon mesh to remove debris. Red blood cells were removed by ammonium chloride treatment. Cells were washed with c-DMEM, counted and diluted to the concentration of $2 \times 10^5$ cells/ml of c-DMEM. At this point, the cell suspension is divided into two parts, one being differentiated into DC, and the other into Mph.

Example 3: Mph and DC Generation and Maturation

For DC differentiation, cells are plated into low-attachment Petri dishes in c-DMEM supplemented with recombinant murine GM-CSF (20 ng/ml), recombinant murine IL-4 (500 U/ml) and beta-ME (50 uM). As the source of GM-CSF the conditioned media of J558L cells, transfected with murine GM-CSF, can be used (at 10% concentration).

For Mph differentiation, cells are plated into culture-treated dishes in c-DMEM supplemented with the same additives as for DC except IL-4.

Both sets of cells are incubated at 37 C in CO2 incubator. On day 3 and day 6 of culture, carefully aspirate 75% media and replace with fresh c-DMEM with supplements (again, except IL-4 for Mph cells). By day 8 both DC and Mph cells are differentiated, this is confirmed by phenotyping (see below). On day 8, collect all floating and few attached DC cells (with EDTA), spin once, plate in fresh Petri dishes in the fresh c-DMEM supplemented with GM-CSF, IL-4, beta-ME at $1 \times 10^6$ cells/ml. Since macrophages are adhered to the plate, aspirate spent media, replace with fresh c-DMEM supplemented with GM-CSF, beta-ME. At this point, irradiated cancer cells are added to both DC and Mph cells.

Phenotyping of differentiated but immature DC and Mphs cells was performed on day 8 using flow cytometry. Flow cytometry of tumor cells was conducted using antibodies against MHC class I, annexin-V-PE and 7-amino-actinomycin D (7-AAD) from BD Pharmingen. CaliBRITE flow cytometry calibration (BD Pharmingen) was used prior to each run and the same instrument settings were used throughout the collection of flow cytometric data. For DC phenotyping, the following antibodies (e-Bioscience): CD11c, MHC class II were used. For Mph phenotyping—CD11b, MHC class II. Isotype control antibodies were included.

Example 5: Maturation of Mph and DC

Irradiated cancer cells are added to DC and Mph plates at day 8 of culture in 1:1 ratio, incubated at 37°C for 10 hrs. At this time, differentiated DC and Mph cells become loaded with cancer cells and its debris. After 10 hr, add TNF-alpha (100 ng/ml) to all DC and Mph dishes for maturation. Incubate cells overnight at 37° ° C. Maturation confirmed by flow cytometry with the following antibodies: for DC— CD80, CD86, CD40, for Mph—CD86, CD115, F4/80. 3 hours prior to collection of matured loaded DC and Mph add LPS (100 ng/ml) and poly I/C (25 ug/ml) to the plates.

Example 6: Vaccination

After 3 hours incubation of loaded DC and Mph cells with LPS and poly I/C all floating cells collected, attached cells collected with EDTA and trypsin, all cells combined, washed twice with PBS, resuspended in sterile saline (0.9%

NaCl) supplemented with LPS (100 ng/ml). At this point, loaded DC and MphH are ready for injection. Mice are injected subcutaneously, 35-40×10° combined DC/Mph per mouse. The injection of the vaccine was done in two formats: therapeutic and preventive. In therapeutic setting, the vaccine was administered intradermally in the left flank in the volume 50 ul 3-5 days after the initiation of tumor. In preventive setting, the vaccine was administered also intradermally in the left flank in the volume 50 ul of PBS at days 14, 8 and 3 prior to the initiation of the tumors.

Example 7: Methods for Assessing Immune Response

Figure 4A:
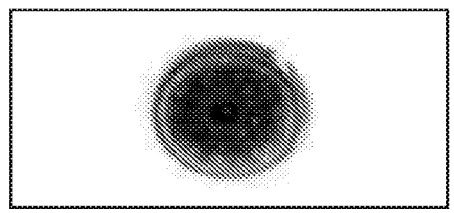
FIG. 4A-FIG. 4D are photographs illustrating ELISPOT analysis of IFN-γ producing splenic T cells from ectopic PaCa mice where
Figure 4C:
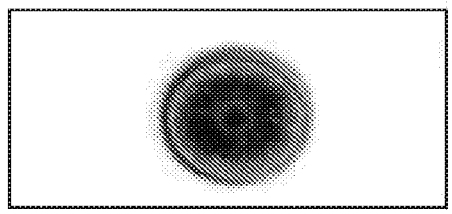
Figure 4B:
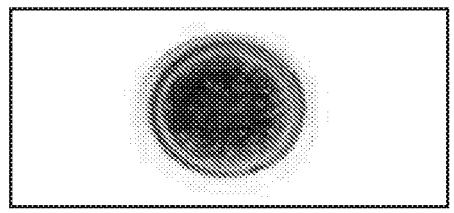
Figure 4D:
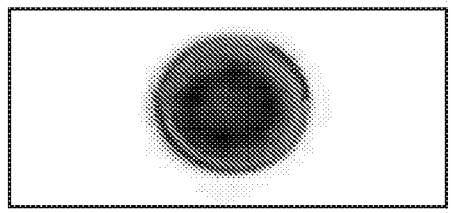

The present disclosure provides ELISPOT assays (FIG. 4A-FIG. 4B) for characterizing immune response (see, e.g., of US 2007/0190029 of Pardoll; Chattopadhyay (2008) Cytometry A. 2008 73:1001-1009; Vollers (2008) Immunology. 123:305-313; Lalvani, et al. (1997) J. Exp. Med. 186:859-865; Waldrop (1997) J. Clin. Invest. 99:1739-1750; Hudgens (2004) J. Immunol. Methods 288:19-34; Goulder (2001) J. Virol. 75:1339-1347; Goulder (2000) J. Exp. Med. 192:1819-1831; Anthony (2003) Methods 29:260-269; Badovinac and Harty (2000) J. Immunol, Methods 238:107-117). Immune response in a patient can be assessed by endpoints that are used in oncology clinical trials, including objective response (RECIST criteria), overall survival, progression-free survival (PFS), disease-free survival, time to distant metastasis, 6-month PFS, 12-month PFS, and so on. The ELISPOT analysis of IFN-γ producing splenic T cells from ectopic pancreatic cancer mice is shown in FIG. 4A-FIG. 4B. FIG. 4A represents tumor-grafted, non-vaccinated, pulsed splenic T cells; FIG. 4B represents tumor grafted, vaccinated, non-pulsed splenic T cells. FIG. 4C represents tumor-grafted, non-vaccinated, non-pulsed splenic T cells and FIG. 4D represents a non-grafted control. An increase in IFN-γ secreting T-lymphocytes was observed in vaccinated mice in comparison to non-vaccinated mice. A person skilled in the art would understand that there are a variety of assay methods to verify that the administration results in generating an immune response. Examples include, but are not limited to, intracellular cytokine staining assays, tetramer assays, antibody titers in patients serum directed against cancer cells in general and certain cancer cell-associated antigens; the ELISPOT test showing the activation and expansion of cancer-specific T-cells, the size of the tumor lesions as per CT scan and/or MRI, the levels of tumor markers (should decrease) in serum, and the cytotoxicity of patient's serum directed against cancer cells in culture etc.

One of ordinary skill in the art can make many variations and modifications to the above-described embodiments of the invention without departing from the spirit or scope of the appended claims. Accordingly, all such variations and modifications are within the scope of the appended claims.

REFERENCES

All citations (e.g., scientific journal publications, patents, and other reference material) mentioned herein are hereby incorporated herein by reference to the same extent as if each individual citation was specifically and individually indicated to be incorporated by reference.

1. Rodrigues C M, Matias B F, Murta E F, Michelin M A. The role of T lymphocytes in cancer patients undergoing immunotherapy with autologous dendritic cells. Clin Med Insights Oncol. 2011; 5:107-15.
2. Matias BF1, de Oliveira T M, Rodrigues C M, Abdalla D R, Montes L, Murta E F, Michelin M A.Clin. Influence of immunotherapy with autologous dendritic cells on innate and adaptive immune response in cancer. Med Insights Oncol. 2013, 7:165-72.
3. da Cunha A, Michelin M A, Murta E F. Pattern response of dendritic cells in the tumor microenvironment and breast cancer. World J Clin Oncol. 2014, 10;5(3):495-502.
4. Aleixo A A, Michelin M A, Murta E F. Immunotherapy with dendritic cells as a cancer treatment: perspectives and therapeutic potential. Recent Pat Endocr Metab Immune Drug Discov. 2013 September;7(3):226-32.
5. Aleixo A A, Michelin M A, Murta E F. Dendritic cell vaccine and cancer treatment: Recent Pat Endocr Metab Immune Drug Discov. 2014 January;8(1):26-9.
6. Wang J, Reiss K A, Khatri R, Jaffee E, Laheru D. Immune Therapy in G I Malignancies: A Review. J Clin Oncol. 2015 Jun. 1; 33(16):1745-53. doi: 10.1200/JCO.2015.60.7879. Epub 2015 Apr. 27.
7. Le D T, Wang-Gillam A, Picozzi V, Greten T F, Crocenzi T, Springett G, Morse M, Zeh H, Cohen D, Fine R L, Onners B, Uram J N, Laheru D A, Lutz E R, Solt S, Murphy A L, Skoble J, Lemmens E, Grous J, Dubensky T Jr, Brockstedt D G, Jaffee E M. Safety and survival with GVAX pancreas prime and *Listeria Monocytogenes*-expressing mesothelin (CRS-207) boost vaccines for metastatic pancreatic cancer. J Clin Oncol. 2015 Apr. 20; 33(12):1325-33. doi: 10.1200/JCO.2014.57.4244. Epub 2015 Jan. 12.
8. Soares K C, Rucki A A, Wu A A, Olino K, Xiao Q, Chai Y, Wamwea A, Bigelow E, Lutz E, Liu L, Yao S, Anders R A, Laheru D, Wolfgang C L, Edil B H, Schulick R D, Jaffee E M, Zheng L. PD-1/P D-L1 blockade together with vaccine therapy facilitates effector T cell infiltration into pancreatic tumors. J Immunother. 2015 January;38 (1):1-11. doi: 10.1097/CJI.0000000000000062.
9. Lutz E R, Wu A A, Bigelow E, Sharma R, Mo G, Soares K, Solt S, Dorman A, Wamwea A, Yager A, Laheru D, Wolfgang C L, Wang J, Hruban R H, Anders R A, Jaffee E M, Zheng L. Immunotherapy converts nonimmunogenic pancreatic tumors into immunogenic foci of immune regulation. Cancer Immunol Res. 2014 July;2(7): 616-31. doi: 10.1158/2326-6066.CIR-14-0027. Epub 2014 Jun. 18.
10. Salman B, Zhou D, Jaffee E M, Edil B H, Zheng L. Vaccine therapy for pancreatic cancer. Oncoimmunology. 2013 Dec. 1; 2(12):e26662. Epub 2013 Oct. 22.
11. Le D T, Lutz E, Uram J N, Sugar E A, Onners B, Solt S, Zheng L, Diaz L A Jr, Donehower R C, Jaffee E M, Laheru D A. Evaluation of ipilimumab in combination with allogeneic pancreatic tumor cells transfected with a G M-CSF gene in previously treated pancreatic cancer. J Immunother. 2013 September;36(7):382-9. doi: 10.1097/CJI.0b013e31829fb7a2.
12. Laheru D, Biedrzycki B, Jaffee E M. Development of a cytokine-modified allogeneic whole cell pancreatic cancer vaccine. Methods Mol Biol. 2013; 980:175-203. doi: 10.1007/978-1-62703-287-2_9.
13. Soares K C, Zheng L, Edil B, Jaffee E M. Vaccines for pancreatic cancer. Cancer J. 2012 November-December; 18(6):642-52. doi: 10.1097/PPO.0b013e3182756903.
14. Lutz E, Yeo C J, Lillemoe K D, Biedrzycki B, Kobrin B, Herman J, Sugar E, Piantadosi S, Cameron J L, Solt S, Onners B, Tartakovsky I, Choi M, Sharma R, Illei P B, Hruban R H, Abrams R A, Le D, Jaffee E, Laheru D. A lethally irradiated allogeneic granulocyte-macrophage colony stimulating factor-secreting tumor vaccine for pancreatic adenocarcinoma. A Phase II trial of safety, efficacy, and immune activation. Ann Surg. 2011 February;253(2):328-35. doi: 10.1097/SLA.0b013e3181fd271c.
15. Laheru D, Lutz E, Burke J, Biedrzycki B, Solt S, Onners B, Tartakovsky I, Nemunaitis J, Le D, Sugar E, Hege K, Jaffee E. Clin Allogeneic granulocyte macrophage colony-stimulating factor-secreting tumor immunotherapy alone or in sequence with cyclophosphamide for metastatic pancreatic cancer: a pilot study of safety, feasibility, and immune activation. Cancer Res. 2008 Mar. 1; 14(5):1455-63. doi: 10.1158/1078-0432.CCR-07-0371.
16. Koido S, Homma S, Okamoto M, Takakura K, Mori M, Yoshizaki S, Tsukinaga S, Odahara S, Koyama S, Imazu H, Uchiyama K, Kajihara M, Arakawa H, Misawa T, Toyama Y, Yanagisawa S, Ikegami M, Kan S, Hayashi K, Komita H, Kamata Y, Ito M, Ishidao T, Yusa S, Shimodaira S, Gong J, Sugiyama H, Ohkusa T, Tajiri H. Treatment with chemotherapy and dendritic cells pulsed with multiple Wilms' tumor 1 (WT1)-specific MHC class I/II-restricted epitopes for pancreatic cancer. Clin Cancer Res. 2014 Aug. 15;20(16):4228-39. doi: 10.1158/1078-0432.CCR-14-0314. Epub 2014 Jul. 23.
17. Koido S, Homma S, Kan S, Takakura K, Namiki Y, Kobayashi H, Ito Z, Uchiyama K, Kajihara M, Arihiro S, Arakawa H, Okamoto M, Ohkusa T, Gong J, Tajiri H. Induction of antigen-specific cytotoxic T lymphocytes by fusion cells generated from allogeneic plasmacytoid dendritic and tumor cells. Int J Oncol. 2014 July;45(1):470-8. doi: 10.3892/ijo.2014.2433. Epub 2014 May 9.
18. Koido S, Homma S, Takahara A, Namiki Y, Tsukinaga S, Mitobe J, Odahara S, Yukawa T, Matsudaira H, Nagatsuma K, Uchiyama K, Satoh K, Ito M, Komita H, Arakawa H, Ohkusa T, Gong J, Tajiri H. Current immunotherapeutic approaches in pancreatic cancer. Clin Dev Immunol. 2011; 2011:267539. doi: 10.1155/2011/267539. Epub 2011 Sep. 14.
19. Koido S, Hara E, Homma S, Namiki Y, Komita H, Takahara A, Nagasaki E, Ito M, Sagawa Y, Mitsunaga M, Uchiyama K, Satoh K, Arihiro S, Ohkusa T, Gong J, Tajiri H. Dendritic/pancreatic carcinoma fusions for clinical use: Comparative functional analysis of healthy-versus patient-derived fusions. Clin Immunol. 2010 June; 135 (3):384-400. doi: 10.1016/j.clim.2010.02.003. Epub 2010 Mar. 11.
20. Coveler A L, Rossi G R, Vahanian N N, Link C, Chiorean E G. Algenpantucel-L immunotherapy in pancreatic adenocarcinoma. Immunotherapy. 2016 February; 8(2):117-25. doi: 10.2217/imt. 15.113. Epub 2016 Jan. 20.
21. McCormick K A, Coveler A L, Rossi G R, Vahanian N N, Link C, Chiorean E G. Pancreatic cancer: Update on Immunotherapies and Algenpantucel-L. Hum Vaccin Immunother. 2015 Nov. 30:0. [Epub ahead of print]
22. Zhang Y, Choi M. Immune Therapy in Pancreatic Cancer: Now and the Future? Rev Recent Clin Trials. 2015; 10(4):317-25.
23. Hardacre J M, Mulcahy M, Small W, Talamonti M, Obel J, Krishnamurthi S, Rocha-Lima C S, Safran H, Lenz H J, Chiorean E G. Addition of algenpantucel-L immunotherapy to standard adjuvant therapy for pancreatic cancer: a phase 2 study. J Gastrointest Surg. 2013 January; 17(1):94-100; discussion p. 100-1. doi: 10.1007/s11605-012-2064-6. Epub 2012 Nov. 15.
24. Dodson L F, Hawkins W G, Goedegebuure P. Potential targets for pancreatic cancer immunotherapeutics. Immunotherapy. 2011 April;3(4):517-37. doi: 10.2217/imt. 11.10.
25. Pappalardo F, Pennisi M, Ricupito A, Topputo F, Bellone M. Induction of T cell memory by a dendritic cell vaccine: a computational model. Bioinformatics. 2014 Jul. 1; 30(13):1884-91. doi: 10.1093/bioinformatics/btu059. Epub 2014 Mar. 6.
26. Ricupito A1, Grioni M, Calcinotto A, Bellone M. Boosting anticancer vaccines: Too much of a good thing? Oncoimmunology. 2013 Jul. 1; 2(7):e25032. Epub 2013 May 16.
27. Ricupito A, Grioni M, Calcinotto A, Hess Michelini R, Longhi R, Mondino A, Bellone M. Booster vaccinations against cancer are critical in prophylactic but detrimental in therapeutic settings. Cancer Res. 2013 Jun. 15; 73(12): 3545-54. doi: 10.1158/0008-5472.CAN-12-2449. Epub 2013 March
28. Forni G, Curcio C, Spadaro M, Iliffe J, Quaglino E, Di Carlo E, Musiani P, Lollini P L. Immunization in tumor prevention. Int Immunopharmacol. 2003 August; 3(8): 1151-8.
29. Forni G. Vaccines for tumor prevention: a pipe dream? J Infect Dev Ctries. 2015 Jul. 4; 9(6):600-8. doi: 10.3855/jidc.7201.
30. Tuohy V K, Jaini R. Prophylactic cancer vaccination by targeting functional non-self. Ann Med. 2011 August;43 (5):356-65. doi: 10.3109/07853890.2011.565065. Epub 2011 Jun. 9.
31. Martín-Fontecha A, Lanzavecchia A, Sallusto F. Dendritic cell migration to peripheral lymph nodes. Handb Exp Pharmacol. 2009; (188):31-49. doi: 10.1007/978-3-540-71029-5_2.
32. Förster R, Braun A, Worbs T. Lymph node homing of T cells and dendritic cells via afferent lymphatics. Trends Immunol. 2012 June;33(6):271-80. doi: 10.1016/j.it.2012.02.007. Epub 2012 Mar. 27.
33. Abediankenari S, Yousefzadeh Y, Azadeh H, Vahedi M. Comparison of several maturation inducing factors in dendritic cell differentiation. Iran J Immunol. 2010 June; 7(2):83-7. doi: IJIv7i2A3.
34. Mikyšková R, Štěpánek I, Indrová M, Bieblová J, Šímová J, Truxová I, Moserová I, Fučíková J, Bartůňková J, Špíšek R, Reiniš M. Dendritic cells pulsed with tumor cells killed by high hydrostatic pressure induce strong immune responses and display therapeutic effects both in murine TC-1 and TRAMP-C2 tumors when combined with docetaxel chemotherapy. Int J Oncol. 2016 March; 48(3):953-64. doi: 10.3892/ijo.2015.3314. Epub 2015 Dec. 29.
35. Podrazil M, Horvath R, Becht E, Rozkova D, Bilkova P, Sochorova K, Hromadkova H, Kayserova J, Vavrova K, Lastovicka J, Vrabcova P, Kubackova K, Gasova Z, Jarolim L, Babjuk M, Spisek R, Bartunkova J, Fucikova J. Phase I/II clinical trial of dendritic-cell based immunotherapy (DCVAC/PCa) combined with chemotherapy in patients with metastatic, castration-resistant prostate cancer. Oncotarget. 2015 Jul. 20; 6(20):18192-205.
36. Bloy N, Pol J, Aranda F, Eggermont A, Cremer I, Fridman W H, Fučíková J, Galon J, Tartour E, Spisek R, Dhodapkar M V, Zitvogel L, Kroemer G, Galluzzi L. Trial watch: Dendritic cell-based anticancer therapy. Oncoimmunology. 2014 Dec. 21; 3(11):e963424. eCollection 2014.
37. Truxova I, Pokorna K, Kloudova K, Partlova S, Spisek R, Fucikova J. Day 3 Poly (I:C)-activated dendritic cells generated in CellGro for use in cancer immunotherapy trials are fully comparable to standard Day 5 DCs. Immunol Lett. 2014 July; 160(1):39-49. doi: 10.1016/j.imlet.2014.03.010. Epub 2014 Apr. 12.

38. Chiang C L, Coukos G, Kandalaft L E. Whole Tumor Antigen Vaccines: Where Are We? Vaccines (Basel). 2015 Apr. 23; 3(2):344-72. doi: 10.3390/vaccines3020344.
39. Chiang C L, Balint K, Coukos G, Kandalaft L E. Potential approaches for more successful dendritic cell-based immunotherapy. Expert Opin Biol Ther. 2015 April; 15(4):569-82. doi: 10.1517/14712598.2015.1000298. Epub 2015 Jan. 2.
40. Chiang C L, Kandalaft L E, Tanyi J, Hagemann A R, Motz G T, Svoronos N, Montone K, Mantia-Smaldone G M, Smith L, Nisenbaum H L, Levine B L, Kalos M, Czerniecki B J, Torigian D A, Powell D J Jr, Mick R, Coukos G. A dendritic cell vaccine pulsed with autologous hypochlorous acid-oxidized ovarian cancer lysate primes effective broad antitumor immunity: from bench to bedside. Clin Cancer Res. 2013 Sep. 1; 19(17):4801-15. doi: 10.1158/1078-0432.CCR-13-1185. Epub 2013 Jul. 9.
41. Kandalaft L E, Chiang C L, Tanyi J, Motz G, Balint K, Mick R, Coukos G. A Phase I vaccine trial using dendritic cells pulsed with autologous oxidized lysate for recurrent ovarian cancer. J Transl Med. 2013 Jun. 18; 11:149. doi: 10.1186/1479-5876-11-149.
42. Nakamura I, Kanazawa M, Sato Y, Irisawa A, Takagi T, Ogata T, Kashimura S, Kenjo A, Suzuki H, Shibata M, Shimura T, Ohira H, Goto M, Takenoshita S, Ohto H. Clinical evaluation of dendritic cells vaccination for advanced cancer patients at Fukushima Medical University. Fukushima J Med Sci. 2012; 58(1):40-8.
43. Irisawa A, Takagi T, Kanazawa M, Ogata T, Sato Y, Takenoshita S, Ohto H, Ohira H. Endoscopic ultrasound-guided fine-needle injection of immature dendritic cells into advanced pancreatic cancer refractory to gemcitabine: a pilot study. Pancreas. 2007 August; 35(2):189-90.
44. Kanzaki N, Terashima M, Kashimura S, Hoshino M, Ohtani S, Matsuyama S, Hoshino Y, Kogure M, Oshibe I, Endo H, Saito T, Yaginuma H, Gotoh M, Ohto H. Understanding the response of dendritic cells to activation by streptococcal preparation OK-432. Anticancer Res. 2005 November-December;25(6B):4231-8.
45. Hirschowitz E A, Foody T, Hidalgo G E, Yannelli J R. Immunization of NSCLC patients with antigen-pulsed immature autologous dendritic cells. Lung Cancer. 2007 September;57(3):365-72. Epub 2007 May 16.
46. Yannelli J R, Sturgill J, Foody T, Hirschowitz E. The large scale generation of dendritic cells for the immunization of patients with non-small cell lung cancer (NSCLC). Lung Cancer. 2005 March;47(3):337-50.
47. Best A, Hidalgo G, Mitchell K, Yannelli J R. Issues concerning the large scale cryopreservation of peripheral blood mononuclear cells (PBMC) for immunotherapy trials. Cryobiology. 2007 June;54(3):294-7. Epub 2007 Feb. 28.
48. Burgdorf S K. Dendritic cell vaccination of patients with metastatic colorectal cancer. Dan Med Bull. 2010 September;57(9):B4171.
49. Gilboa E. DC-based cancer vaccines. J Clin Invest. 2007 May; 117(5): 1195-203.
50. Gilboa E, Vieweg J. Cancer immunotherapy with mRNA-transfected dendritic cells. Immunol Rev. 2004 June; 199:251-63.
51. Morse M A, Nair S K, Mosca P J, Hobeika A C, Clay T M, Deng Y, Boczkowski D, Proia A, Neidzwiecki D, Clavien P A, Hurwitz H I, Schlom J, Gilboa E, Lyerly H K. Immunotherapy with autologous, human dendritic cells transfected with carcinoembryonic antigen mRNA. Cancer Invest. 2003 June;21(3):341-9.
52. Heiser A, Coleman D, Dannull J, Yancey D, Maurice M A, Lallas C D, Dahm P, Niedzwiecki D, Gilboa E, Vieweg J. Autologous dendritic cells transfected with prostate-specific antigen RNA stimulate CTL responses against metastatic prostate tumors. J Clin Invest. 2002 February; 109(3):409-17.
53. Gilboa E, Nair S K, Lyerly H K. Immunotherapy of cancer with dendritic-cell-based vaccines. Cancer Immunol Immunother. 1998 April; 46(2):82-7.
54. Nair S K, Snyder D, Rouse B T, Gilboa E. Regression of tumors in mice vaccinated with professional antigen-presenting cells pulsed with tumor extracts. Int J Cancer. 1997 Mar. 17; 70(6):706-15.
55. Schlom J, Hodge J W, Palena C, Tsang K Y, Jochems C, Greiner J W, Farsaci B, Madan R A, Heery C R, Gulley J L. Therapeutic cancer vaccines. Adv Cancer Res. 2014; 121:67-124. doi: 10.1016/B978-0-12-800249-0.00002-0.
56. Amedei A, Niccolai E, Prisco D. Pancreatic cancer: role of the immune system in cancer progression and vaccine-based immunotherapy. Hum Vaccin Immunother. 2014; 10(11):3354-68. doi: 10.4161/hv.34392.
57. Nair S, Archer G E, Tedder T F. Isolation and generation of human dendritic cells. Curr Protoc Immunol. 2012 November; Chapter 7: Unit 7.32. doi: 10.1002/0471142735.im0732s99.
58. U.S. Pat. No. 8,614,093 Pharmaceutical composition for treating or preventing cancer by inducing dendritic cell-like differentiation from monocytes to improve anticancer immune activity
59. U.S. Pat. No. 8,597,946 Enhanced dendritic cells for cancer immunotherapy
60. U.S. Pat. No. 7,846,446 Multi-epitope peptide-loaded dendritic cell immunotherapy for cancer
61. U.S. Pat. No. 6,440,735 Dendritic cell vaccine containing telomerase reverse transcriptase for the treatment of cancer
62. U.S. Pat. No. 5,788,963 Isolation and/or preservation of dendritic cells for prostate cancer immunotherapy
63. U.S. Pat. No. 8,613,916 Immunotherapy for pancreatic cancer
64. U.S. Pat. No. 8,778,361 Canine tumor cell and allogeneic dendritic cell fused vaccine and method for preparing the same
65. U.S. Pat. No. 8,324,369 Dendritic cell vaccine compositions and uses of same
66. U.S. Pat. No. 7,981,673 Process for the maturation of dendritic cells and a vaccine
67. U.S. Pat. No. 6,440,735 Dendritic cell vaccine containing telomerase reverse tr26
68. U.S. Pat. No. 8,597,946 Enhanced dendritic cells for cancer immunotherapy anscriptase fo3
69. U.S. Pat. No. 8,932,575 Compositions and methods for inducing migration by dendritic cells and an immune response
70. U.S. Pat. No. 8,921,104 Method for producing dendritic cells for the treatment of cancer
71. U.S. Pat. No. 8,741,639 Method for producing dendritic cell
72. U.S. Pat. No. 8,574,901 Cryoconserved mature dendritic cells
73. U.S. Pat. No. 8,236,562 Method for producing ready to use, antigen-loaded or unloaded, cryoconserved mature dendritic cells
74. U.S. Pat. No. 8,232,100 Method for producing dendritic cells 75. U.S. Pat. No. 8,129,183 Method for stimulating dendritic cells and cell product thus obtained for the autologous immunotherapy of solid human tumours
76. U.S. Pat. No. 7,981,673 Process for the maturation of dendritic cells and a vaccine
77. U.S. Pat. No. 7,959,934 Method for rapid generation of mature dendritic cells
78. U.S. Pat. No. 7,785,583 In situ maturation of dendritic cells
79. U.S. Pat. No. 7,781,213 Method for producing dendritic cells
80. U.S. Pat. No. 7,566,568 Method for generating highly active human dendritic cells from peripheral blood mononuclear cells
81. U.S. Pat. No. 6,558,951 Maturation of dendritic cells with immune response modifying compounds
82. U.S. Pat. No. 6,524,855 Methods for inducing the differentiation of monocytes into functional dendritic cells
83. U.S. Pat. No. 6,498,034 Method of producing dendritic cells

What is claimed is:

1. A method of stimulating an immune response against a cancer cell-specific antigen in an identified cancer in a subject at risk of having the identified cancer, comprising:
co-administering to the subject an immunologically effective amount of
(a) a whole cancer cell antigen-loaded dendritic cells isolated from a first population of white blood cells cultured under a first set of culture conditions, and
(b) a whole cancer cell antigen-loaded macrophages isolated from a second population of white blood cells cultured under a second set of culture conditions,
wherein the white blood cells are each autologous to the subject, and the whole cancer cell antigen-loaded dendritic cells and the whole cancer cell antigen-loaded macrophages have internalized by phagocytosis a whole cancer cell of the identified cancer in vitro.

2. The method of claim 1, wherein the first set of culture conditions comprise culture medium with GM-CSF, IL4, TNF-α, IL-6 and PGE-2 and the second set of culture conditions comprise culture medium with M-CCF, LPS and TNF-α.

3. The method of claim 1, wherein the whole cancer cell is isolated from the identified cancer in the subject (autologous) or is obtained from a cancer cell line of the identified cancer (allogeneic).

4. The method of claim 3, wherein the whole cancer cell isolated from the identified cancer in the subject or the cancer cell line of the identified cancer is attenuated or killed.

5. The method of claim 4, wherein the whole cancer cell or the cancer cell line is attenuated by irradiation, heat shock, cold shock, glucose deprivation, oxygen deprivation, exposure to at least one drug that alters cell metabolism, or exposure to at least one cytotoxic drug.

6. The method of claim 1, wherein the whole cancer cell antigen-loaded dendritic cells and whole cancer cell antigen-loaded macrophages are combined in a single formulation or separated into individual formulations.

7. The method of claim 6, wherein the individual formulations are administered concurrently or within 24 hours of each other.

8. The method of claim 7, wherein administration of said individual formulations comprises injections of the whole cancer cell antigen-loaded dendritic cells and the whole cancer cell antigen-loaded macrophages weekly for one to three months and then monthly for a subsequent one to five months.

9. The method of claim 1, further comprising administering to the subject a cytokine, a lymphokine, a check-point inhibitor, or a combination thereof.

10. The method of claim 1, wherein said whole cancer cell antigen-loaded dendritic cells and the whole cancer cell antigen-loaded macrophages are administered by subcutaneous, intradermal or intramuscular injection.

11. The method of claim 6, wherein the single formulation is disposed in a containment device or the separate formulations are disposed in two or more containment devices, wherein the containment device or devices are, optionally, used for administration.

12. The method of claim 1, wherein the immune response comprises one or more of a CD4+ T cell response, a CD8+ T cell response, and a B cell response.

13. The method of claim 12, further comprising determining the CD4+ T cell response, the CD8+ T cell response, or the B cell response by ELISPOT assays, by intracellular cytokine staining assays, by tetramer assays, or by detecting antigen-specific antibody production.

14. The method of claim 1, wherein the identified cancer is melanoma, colon cancer, duodenal cancer, prostate cancer, breast cancer, ovarian cancer, ductal cancer, hepatic cancer, pancreatic cancer, liver cancer, renal cancer, endometrial cancer, testicular cancer, stomach cancer, sarcoma, dysplastic oral mucosa, polyposis, thyroid cancer, cervical cancer, head and neck cancer, invasive oral cancer, non-small cell lung carcinoma, small-cell lung carcinoma, mesothelioma, transitional and squamous cell urinary carcinoma, brain cancer, neuroblastoma, or glioma.

15. The method of claim 1, wherein the identified cancer is pancreatic cancer.

16. The method of claim 3, wherein the cancer cell line is pancreatic cell line CFPAC-1, Capan-2, MIA-PaCa-2, BxPC3, Hs766t, Panc 03.27, Panc 02.13, Panc 10.05, Panc 10.05-GMCSF, Panc 05.04, HPAC, HPAF-II, PANC-1, PL45, UACC-462, or PANC 04.03.

* * * * *